United States Patent
Yan et al.

(10) Patent No.: US 11,654,194 B2
(45) Date of Patent: May 23, 2023

(54) PD-L1 ANTIBODY PHARMACEUTICAL COMPOSITION AND USE THEREOF

(71) Applicants: Jiangsu Hengrui Medicine Co., Ltd., Lianyungang (CN); Shanghai Hengrui Pharmaceutical Co., Ltd., Shanghai (CN)

(72) Inventors: Zhen Yan, Shanghai (CN); Jianjian Yang, Shanghai (CN); Xiaodan Yan, Shanghai (CN); Shan Wu, Shanghai (CN); Xun Liu, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 381 days.

(21) Appl. No.: 16/614,148

(22) PCT Filed: May 15, 2018

(86) PCT No.: PCT/CN2018/086866
§ 371 (c)(1),
(2) Date: Nov. 15, 2019

(87) PCT Pub. No.: WO2018/210230
PCT Pub. Date: Nov. 22, 2018

(65) Prior Publication Data
US 2020/0069800 A1 Mar. 5, 2020

(30) Foreign Application Priority Data
May 16, 2017 (CN) .......................... 201710341680.7

(51) Int. Cl.
*A61K 39/395* (2006.01)
*A61K 47/26* (2006.01)
*C07K 16/28* (2006.01)
*A61K 47/12* (2006.01)

(52) U.S. Cl.
CPC ........ *A61K 39/39591* (2013.01); *A61K 47/12* (2013.01); *A61K 47/26* (2013.01); *C07K 16/2827* (2013.01); *C07K 2317/24* (2013.01); *C07K 2317/565* (2013.01); *C07K 2317/76* (2013.01)

(58) Field of Classification Search
CPC ... C07K 16/28; A61K 39/39591; A61K 47/26
See application file for complete search history.

(56) References Cited

U.S. PATENT DOCUMENTS

| 10,815,304 B2 | 10/2020 | Qu et al. |
| 2016/0319022 A1* | 11/2016 | Yang ..................... A61P 29/00 |
| 2018/0339045 A1 | 11/2018 | Li |

FOREIGN PATENT DOCUMENTS

| CN | 103429264 | 12/2013 | |
| CN | 105793288 | 7/2016 | |
| CN | 105960415 | 9/2016 | |
| CN | 107198773 | 9/2017 | |
| JP | 2011256206 | 12/2011 | |
| TW | 201542225 | 11/2015 | |
| TW | 201711699 | 4/2017 | |
| WO | WO-9856418 A1 * | 12/1998 | ....... A61K 39/39591 |
| WO | WO 2007/005874 | 1/2007 | |
| WO | WO2011/066389 | 6/2011 | |
| WO | WO 2010/077634 | 7/2012 | |
| WO | WO 2017084495 | 5/2017 | |

OTHER PUBLICATIONS

International Search Report and Written Opinion of PCT/CN2018/086866 dated Aug. 20, 2018, English Translation, 11 pages.
Taiwan Patent Rejection Decision issued in Taiwan Patent Application No. 107116620, dated Jul. 17, 2019, English Translation, 5 pages.
Taiwan Office Action issued in Taiwan Patent Application No. 107116620, dated Mar. 28, 2019, English Translation, 8 pages.
Chavez et al., "Improved stability of a Model IgG3 by DoE-based evaluation of buffer formulations," Biomed Res. Int., Jan. 2016, 2016:1-8.
Goldberg et al., "Formulation development of therapeutic monoclonal antibodies using high-throughput fluorescence and static light scattering techniques: Role of conformational and colloidal stability," Journal of Pharm. Sciences., Oct. 2010, 100:4:1306-1315.

* cited by examiner

*Primary Examiner* — Prema M Mertz
(74) *Attorney, Agent, or Firm* — Fish & Richardson P.C.

(57) ABSTRACT

The present invention provides a PD-L1 antibody pharmaceutical composition and use thereof. In particular, the present invention provides a pharmaceutical composition comprising the PD-L1 antibody or an antigen-binding fragment thereof in a succinate buffer. In addition, the pharmaceutical composition may also contain a sugar and a non-ionic surfactant.

14 Claims, 1 Drawing Sheet
Specification includes a Sequence Listing.

PD-L1 ANTIBODY PHARMACEUTICAL COMPOSITION AND USE THEREOF

The present application claims priorities of the Chinese Patent Application No. CN201710341680.7 filed on May 16, 2017, the contents of which are incorporated herein by reference in their entireties.

FIELD OF INVENTION

The present disclosure relates to the field of pharmaceutical preparations, in particular to a pharmaceutical composition comprising an anti-PD-L1 antibody or antigen-binding fragment thereof, and a use thereof as an anticancer drug.

BACKGROUND OF THE INVENTION

Programmed death-1 (PD-1), a protein receptor expressed on the surface of T cells and discovered in 1992, is involved in the process of apoptosis. PD-1 has two ligands, namely PD-L1 and PD-L2. PD-L1 is mainly expressed on T cells, B cells, macrophages, and dendritic cells (DCs), and the expression on activated cells can be up-regulated. The expression of PD-L2 is relatively limited, which is mainly expressed on antigen presenting cells, such as activated macrophages and dendritic cells.

PD-L1 inhibits the immune system by binding to PD-1 and B7-1, and many tumor cells in tumor microenvironment express PD-L1. Recent studies have found that high expression of PD-L1 protein in human tumor tissues such as breast cancer, lung cancer, stomach cancer, intestinal cancer, renal cancer, melanoma cancer, non-small cell lung cancer, colon cancer, bladder cancer, ovarian cancer, pancreatic cancer, liver cancer and the others, and the expression level of PD-L1 is closely related to the clinical condition and prognosis of patients. Since PD-L1 acts as a second signaling pathway to inhibit T cell proliferation, blocking the binding between PD-L1/PD-1 has become a very promising emerging target in the field of tumor immunotherapy.

Compared with other chemical drugs, the antibody drugs become unstable due to their larger molecular weight, more complicated structure, and easy degradation, polymerization, or undesired chemical modification. In order to make antibody molecules suitable for administration, and to maintain stability during storage and subsequent use and exert better effects, studies on the preparation of the antibody drugs are particularly important.

A number of multinational pharmaceutical companies are currently developing pharmaceutical compositions containing PD-L1/PD-1 antibodies, such as CN105793288A, CN103429264A, and CN105960415A.

The present disclosure provides a pharmaceutical composition comprising an anti-PD-L1 antibody or antigen-binding fragment thereof which is sufficiently stable and suitable for administration.

SUMMARY OF THE INVENTION

The present disclosure provides a pharmaceutical composition comprising an anti-PD-L1 antibody or antigen-binding fragment thereof and a buffer, wherein the buffer is preferably a succinate buffer or an acetate buffer, more preferably a succinate buffer.

In the embodiments of the present disclosure, the concentration of the buffer is about 5 mM to 50 mM, preferably about 10 mM to 30 mM, more preferably 10 mM to 20 mM; non-limiting embodiments of the concentration of the buffer include 10 mM, 12 mM, 14 mM, 16 mM, 18 mM and 20 mM.

In the embodiments of the present disclosure, the pH of the pharmaceutical composition is about 4.5 to 6.0, preferably about 4.8 to 5.7, more preferably 5.0 to 5.5, and can be 5.0, 5.1, 5.2, 5.3, 5.4 or 5.5.

In the embodiments of the present disclosure, the concentration of the antibody in the pharmaceutical composition is about 30 mg/mL to about 80 mg/mL, preferably about 40 mg/mL to about 60 mg/mL, more preferably 45 mg/mL to about 55 mg/mL; non-limiting embodiments of the concentration of the antibody include 45 mg/mL, 46 mg/mL, 47 mg/mL, 48 mg/mL, 49 mg/mL, 50 mg/mL, 51 mg/mL, 52 mg/mL, 53 mg/mL, 54 mg/mL and 55 mg/mL.

Further, the pharmaceutical composition of the present disclosure also comprises a saccharide. The "saccharide" of the present disclosure comprises the conventional composition $(CH_2O)_n$ and the derivatives thereof, including monosaccharide, disaccharide, trisaccharide, polysaccharide, sugar alcohol, reducing sugar, non-reducing sugar and the like, which can be selected from the group consisting of glucose, sucrose, trehalose, lactose, fructose, maltose, dextran, glycerol, dextran, erythritol, glycerol, arabitol, xylitol, sorbitol, mannitol, melibiose, melezitose, melitriose, mannotriose, stachyose, maltose, lactulose, maltulose, sorbitol, maltitol, lactitol, isomaltulose and the like. The saccharide is preferably non-reducing disaccharide, more preferably trehalose or sucrose.

In the embodiments of the present disclosure, the concentration of the saccharide in the pharmaceutical composition is about 30 mg/mL to about 90 mg/mL, preferably 50 mg/mL to about 70 mg/mL, more preferably 55 mg/mL to about 65 mg/mL; non-limiting embodiments of the concentration of the saccharide include 55 mg/mL, 57 mg/mL, 59 mg/mL, 60 mg/mL, 61 mg/mL, 63 mg/mL and 65 mg/mL.

Further, the pharmaceutical composition also comprises a surfactant, which can be selected from the group consisting of polysorbate 20, polysorbate 80, poloxamer, Triton, sodium dodecyl sulfate, sodium lauryl sulfonate, sodium octyl glycoside, lauryl-sulfobetaine, myristyl-sulfobetaine, linoleyl-sulfobetaine, or stearyl-sulfobetaine, lauryl-sarcosine, myristyl-sarcosine, linoleyl-sarcosine, stearyl-sarcosine, linoleyl-betaine, myristyl-betaine, cetyl-betaine, lauryl amidopropyl-betaine, cocaramidopropyl-betaine, linoleamidopropyl-betaine, myristamidopropyl-betaine, palmitoylamidopropyl-betaine, or isostearamidopropyl-betaine, myristamidopropyl-dimethylamine, palmitoylamidopropyl-dimethylamine, isostearamidopropyl-dimethylamine, sodium methyl cocoyl-taurate, or dissodium methyl oleyl-taurate, polyethylene glycol, polypropylene glycol, and copolymer of ethylene and propylene glycol, etc. The surfactant is preferably polysorbate 80 or polysorbate 20, more preferably polysorbate 80.

In the embodiments of the present disclosure, the concentration of the surfactant in the pharmaceutical composition is about 0.1 mg/mL to 1.0 mg/mL, preferably 0.2 mg/mL to 0.8 mg/mL, more preferably 0.4 mg/mL to 0.8 mg/mL; non-limiting embodiments of the concentration of the surfactant include 0.1 mg/mL, 0.2 mg/mL, 0.3 mg/mL, 0.4 mg/mL, 0.5 mg/mL, 0.6 mg/mL, 0.7 mg/mL and 0.8 mg/mL.

In the embodiments of the present disclosure, wherein the antibody or the antigen-binding fragment thereof in the pharmaceutical composition comprises any one of the CDR region sequences or mutant sequences thereof selected from the group consisting of: antibody heavy chain variable region HCDR sequence: SEQ ID NO: 1-3, SEQ ID NO: 7-9; and/or, antibody light chain variable region LCDR sequences: SEQ ID NO: 4-6, SEQ ID NO: 10-12; specifically as follows:

```
HCDR1 is selected from:
                            SEQ ID NO: 1
NDYWX₁
or
                            SEQ ID NO: 7
SYWMH, HCDR2 is selected from:
                            SEQ ID NO: 2
YISYTGSTYYNPSLKS
or
                            SEQ ID NO: 8
RIX₄PNSG X₅TSYNEKFKN,
and/or HCDR3 is selected from:
                            SEQ ID NO: 3
SGGWLAPFDY
or
                            SEQ ID NO: 9
GGSSYDYFDY;
and/or LCDR1 is selected from:
                            SEQ ID NO: 4
KSSQSLFY X₂ SNQK X₃SLA
or
                            SEQ ID NO: 10
RASESVSIHGTHLMH, LCDR2 is selected from:
                            SEQ ID NO: 5
GASTRES
or
                            SEQ ID NO: 11
AASNLES,
and/or LCDR3 is selected from:
                            SEQ ID NO: 6
QQYYGYPYT
or
                            SEQ ID NO: 12
QQSFEDPLT;
``` wherein, $X_1$ is selected from N or T, $X_2$ is selected from R or H, $X_3$ is selected from N or H, $X_4$ is selected from H or G, and $X_5$ is selected from G or F.

In the embodiments of the present disclosure, preferably, the antibody or the antigen-binding fragment thereof in the pharmaceutical composition comprises a light chain variable region CDR sequence selected from the group consisting of: SEQ ID NO: 10, SEQ ID NO: 11, SEQ ID NO: 12 or a mutated sequence thereof, and a heavy chain variable region CDR sequence selected from the group consisting of: SEQ ID NO: 7, SEQ ID NO: 8 and SEQ ID NO: 9 or a mutant sequence thereof; more preferably, the antibody or the antigen-binding fragment thereof comprises LCDR1, LCDR2 and LCDR3 sequences as shown in SEQ ID NO: 10, SEQ ID NO: 11 and SEQ ID NO: 12, respectively, and HCDR1, HCDR2 and HCDR3 sequences as shown in SEQ ID NO: 7, SEQ ID NO: 8 and SEQ ID NO:9, respectively;

or, preferably, the antibody or the antigen-binding fragment thereof in the pharmaceutical composition comprises a heavy chain variable region CDR sequence selected from the group consisting of: SEQ ID NO: 1, SEQ ID NO: 2, SEQ ID NO: 3 or a mutated sequence thereof, and a light chain variable region CDR sequence selected from the group consisting of: SEQ ID NO: 4, SEQ ID NO: 5 and SEQ ID NO: 6 or a mutant sequence thereof; more preferably, the antibody or the antigen-binding fragment thereof comprises HCDR1, HCDR2 and HCDR3 sequences as shown in SEQ ID NO: 1, SEQ ID NO: 2 and SEQ ID NO: 3, respectively, and LCDR1, LCDR2 and LCDR3 sequences as shown in SEQ ID NO: 4, SEQ ID NO: 5 and SEQ ID NO: 6, respectively.

In the embodiments of the present disclosure, the antibody or the antigen-binding fragment thereof in the pharmaceutical composition comprises a light chain variable region CDR sequence having at least 85%, 86%, 87%, 88%, 89%, 90%, 91%, 92%, 93%, 94%, 95%, 96%, 97%, 98%, or 99% sequence identity to the amino acid sequences as shown in SEQ ID NO: 10, SEQ ID NO: 11 and SEQ ID NO: 12, and a heavy chain variable region CDR sequence having at least 85%, 86%, 87%, 88%, 89%, 90%, 91%, 92%, 93%, 94%, 95%, 96%, 97%, 98%, or 99% sequence identity to the amino acid sequences as shown in SEQ ID NO: 7, SEQ ID NO: 8 and SEQ ID NO: 9.

In the embodiments of the present disclosure, wherein the antibody or the antigen-binding fragment thereof in the pharmaceutical composition can be selected from the group consisting of a murine antibody, a chimeric antibody, a humanized antibody and a human antibody, preferably a humanized antibody.

In the embodiments of the present disclosure, wherein the antibody or the antigen-binding fragment thereof in the pharmaceutical composition comprises a heavy chain variable region sequence having at least 85%, 86%, 87%, 88%, 89%, 90%, 91%, 92%, 93%, 94%, 95%, 96%, 97%, 98%, or 99% sequence identity to the amino acid sequence as shown in SEQ ID NO: 13, and a light chain variable region sequence having at least 85%, 86%, 87%, 88%, 89%, 90%, 91%, 92%, 93%, 94%, 95%, 96%, 97%, 98%, or 99% sequence identity to the amino acid sequence as shown in SEQ ID NO: 14.

In the embodiments of the present disclosure, the antibody or the antigen-binding fragment thereof in the pharmaceutical composition comprises a heavy chain variable region sequence having at least 85%, 86%, 87%, 88%, 89%, 90%, 91%, 92%, 93%, 94%, 95%, 96%, 97%, 98%, or 99% sequence identity to the amino acid sequence as shown in SEQ ID NO: 15, and a light chain variable region sequence having at least 85%, 86%, 87%, 88%, 89%, 90%, 91%, 92%, 93%, 94%, 95%, 96%, 97%, 98%, or 99% sequence identity to the amino acid sequence as shown in SEQ ID NO: 17.

The present disclosure further provides a pharmaceutical composition comprising an anti-PD-L1 antibody or an antigen-binding fragment thereof having a concentration of about 30 mg/mL to about 80 mg/mL, a succinate buffer at pH 5.0-6.0 having a concentration of about 5 mM to about 50 mM, a disaccharide having a concentration of from about 30 mg/mL to about 90 mg/mL, and a polysorbate 80 having a concentration of from about 0.1 mg/mL to about 1.0 mg/mL.

The present disclosure further provides a pharmaceutical composition comprising 40 mg/mL-60 mg/mL anti-PD-L1 antibody or antigen-binding fragment thereof, 10 mM-30 mM succinate buffer at pH 5.0-5.5, 40 mg/mL-80 mg/mL sucrose and 0.4 mg/mL-0.8 mg/mL polysorbate 80.

The present disclosure further provides a pharmaceutical composition comprising 45 mg/mL-55 mg/mL PD-L1 antibody or antigen-binding fragment thereof, 10 mM-20 mM succinate buffer at pH 5.0-5.5, 55 mg/mL-65 mg/mL sucrose and 0.5 mg/mL-0.7 mg/mL polysorbate 80.

The present disclosure further provides a pharmaceutical composition comprising an anti-PD-L1 antibody or antigen-binding fragment thereof having a concentration of about 30 mg/mL to about 80 mg/mL, an acetate buffer at pH 5.0-6.0 having a concentration of about 5 mM to about 50 mM, a disaccharide having a concentration of about 30 mg/mL to about 90 mg/mL, and a polysorbate 80 having a concentration of about 0.1 mg/mL to about 1.0 mg/mL.

The present disclosure further provides a pharmaceutical composition comprising 50 mg/mL anti-PD-L1 antibody or antigen-binding fragment thereof, 10 mM succinate buffer at pH 5.3 and 60 mg/mL sucrose.

The present disclosure further provides a pharmaceutical composition comprising 50 mg/mL anti-PD-L1 antibody or antigen-binding fragment thereof, 10 mM acetate buffer at pH 5 and 90 mg/mL sucrose.

The present disclosure further provides a pharmaceutical composition comprising 50 mg/mL anti-PD-L1 antibody or antigen-binding fragment thereof, 30 mM acetate buffer at pH 5 and 60 mg/mL of trehalose.

The present disclosure further provides a pharmaceutical composition comprising 50 mg/mL anti-PD-L1 antibody or antigen-binding fragment thereof, 30 mM acetate buffer at pH 5 and 60 mg/mL of trehalose.

The present disclosure further provides a pharmaceutical composition comprising 50 mg/mL anti-PD-L1 antibody or antigen-binding fragment thereof, 30 mM acetate buffer at pH 5.6 and 90 mg/mL sucrose.

The present disclosure further provides a pharmaceutical composition comprising 50 mg/mL anti-PD-L1 antibody or antigen-binding fragment thereof, 10 mM succinate buffer at pH 5.0-5.5, 60 mg/mL sucrose and 0.2 mg/mL polysorbate 20.

The present disclosure further provides a pharmaceutical composition comprising 50 mg/mL anti-PD-L1 antibody or antigen-binding fragment thereof, 10 mM-20 mM succinate buffer at pH 5.2, 60 mg/mL sucrose and 0.2 mg/mL polysorbate 20.

The present disclosure further provides a pharmaceutical composition comprising 50 mg/mL PD-L1 antibody or antigen-binding fragment thereof, 20 mM acetate buffer at pH 5.2, 60 mg/mL sucrose and 0.1 mg/mL-0.3 mg/mL polysorbate 20.

The present disclosure further provides a pharmaceutical composition comprising 50 mg/mL PD-L1 antibody or antigen-binding fragment thereof, 20 mM acetate buffer at pH 5.2, 60 mg/mL sucrose and 0.1 mg/mL-0.3 mg/mL polysorbate 80.

The present disclosure further provides a pharmaceutical composition comprising 50 mg/mL PD-L1 antibody or antigen-binding fragment thereof, 20 mM succinate buffer at pH 5.2, 60 mg/mL sucrose and 0.2 mg/mL-0.6 mg/mL polysorbate 20.

The present disclosure further provides a pharmaceutical composition comprising 50 mg/mL PD-L1 antibody or antigen-binding fragment thereof, 20 mM succinate buffer at pH 5.2, 60 mg/mL sucrose and 0.4-0.8 mg/mL polysorbate 80.

The present disclosure further provides a pharmaceutical composition comprising 50 mg/mL PD-L1 antibody or antigen-binding fragment thereof, 20 mM succinate buffer at pH 5.2, 60 mg/mL sucrose and 0.4 mg/mL polysorbate 80.

The present disclosure further provides a pharmaceutical composition comprising 50 mg/mL PD-L1 antibody or antigen-binding fragment thereof, 20 mM succinate buffer at pH 5.2, 60 mg/mL sucrose and 0.6 mg/mL polysorbate 80.

The present disclosure further provides a pharmaceutical composition comprising 50 mg/mL PD-L1 antibody or antigen-binding fragment thereof, 20 mM succinate buffer at pH 5.2, 60 mg/mL sucrose and 0.8 mg/mL polysorbate 80.

In some embodiments, the concentration of the succinate buffer in the pharmaceutical composition is about 5 mM to 50 mM. In some embodiments, the concentration of the succinate buffer in the pharmaceutical composition is about 10 mM to 30 mM. In some embodiments, the concentration of the succinate buffer in the pharmaceutical composition is about 20 mM.

In some embodiments, the concentration of the acetate buffer in the pharmaceutical composition is about 5 mM to 50 mM. In some embodiments, the concentration of the acetate buffer in the pharmaceutical composition is about 10 mM to 30 mM. In some embodiments, the concentration of the acetate buffer in the pharmaceutical composition is about 20 mM.

In some embodiments, the pH of the pharmaceutical composition is about 5.0 to 6.0. In some embodiments, the pH of the pharmaceutical composition is about 5.0 to 5.5. In some embodiments, the pH of the pharmaceutical composition is 5.2 or 5.5.

In some embodiments, the concentration of the antibody in the pharmaceutical composition is about 30 mg/mL to about 80 mg/mL. In some embodiments, the concentration of the antibody in the pharmaceutical composition is about 40 mg/mL to about 60 mg/mL. In some embodiments, the concentration of the antibody in the pharmaceutical composition is about 50 mg/mL.

In some embodiments, the concentration of the disaccharide in the pharmaceutical composition is about 30 mg/mL to about 90 mg/mL. In some embodiments, the concentration of the disaccharide in the pharmaceutical composition is about 40 mg/mL to about 80 mg/mL. In some embodiments, the concentration of the disaccharide in the pharmaceutical composition is about 60 mg/mL.

In some embodiments, the polysorbate in the pharmaceutical composition is polysorbate 20 or polysorbate 80. In some embodiments, the polysorbate in the pharmaceutical composition is polysorbate 80. In some embodiments, the concentration of the polysorbate in the pharmaceutical composition is about 0.1 mg/mL to 1.0 mg/mL. In some embodiments, the concentration of the polysorbate in the pharmaceutical composition is about 0.4 mg/mL to 0.8 mg/mL. In some embodiments, the concentration of the polysorbate in the pharmaceutical composition is about 0.6 mg/mL.

In some embodiments, the preparation is stable at 2-8° C. for at least 3 months, at least 6 months, at least 12 months, at least 18 months, or at least 24 months. In some embodiments, the preparation is stable at 40° C. for at least 7 days, at least 14 days or at least 28 days.

The present disclosure further provides an article or a kit comprising a container containing any of the stable pharmaceutical compositions described herein. In some embodiments, the container is a glass vial, and the glass vial is a neutral borosilicate glass vial for injection.

The present disclosure further provides a method for preparing the pharmaceutical compositions described above, comprising mixing an anti-PD-L1 antibody or an antigen-binding fragment thereof with a pharmaceutically acceptable excipient.

The present disclosure further provides a use of the pharmaceutical composition described above in manufacturing a medicament for treating a PD-L1-mediated disease or condition, wherein the disease or condition is preferably a cancer; more preferably PD-L1 expressing cancer; most preferably breast cancer, lung cancer, stomach cancer, intestinal cancer, renal cancer, melanoma or non-small cell lung cancer; further more preferably non-small cell lung cancer, melanoma, bladder cancer or renal cancer.

The present disclosure further provides a method for treating or preventing a PD-L1 mediated disease or condition, comprising administering a therapeutically effective amount of the pharmaceutical composition comprising an anti-PD-L1 antibody or antigen-binding fragment thereof to a subject in need thereof; wherein, the disease is preferably a cancer; more preferably PD-L1-expressing cancer; the cancer is most preferably breast cancer, lung cancer, stomach cancer, intestinal cancer, renal cancer, melanoma, non-small cell lung cancer or bladder cancer; most preferably non-small cell lung cancer, melanoma, bladder cancer or renal cancer.

It is appreciated that one, some, or all of the features of the various embodiments described herein can be further combined to obtain other embodiments of the present disclosure. Other embodiments obtained by the combination of the above embodiments of the present disclosure are further described by the following detailed description.

DETAILED DESCRIPTION OF THE INVENTION

Terms

Figure 1:
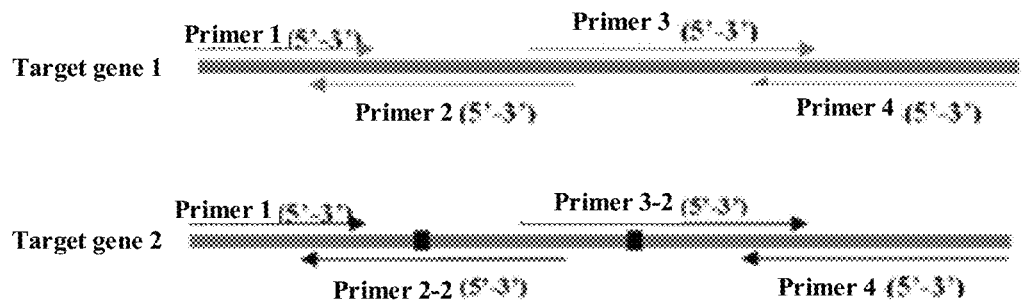
FIG. 1: The schematic diagram of primer design during humanized clone construction.

In order to make the disclosure more readily understood, certain technical and scientific terms are specifically defined below. Unless specifically defined otherwise in this document, all other technical and scientific terms used herein shall be taken to have the same meaning as commonly understood by one of ordinary skill in the art to which this disclosure belongs.

"Buffer" refers to a buffer that is resistant to changes in pH because of its conjugate acid-base component. The pH value of the buffer of the present disclosure is about 4.5 to 6.0, preferably about 5.0 to 6.0, more preferably about 5.0 to 5.5, most preferably 5.2. Examples of the buffer which controls the pH in such range include acetate buffer, succinate buffer, gluconate buffer, histidine buffer, oxalate buffer, lactate buffer, phosphate buffer, citrate buffer, tartrate buffer, fumarate buffer, glycylglycine and other organic acid buffers. The buffer of the present disclosure is preferably succinate buffer or acetate buffer, more preferably succinate buffer.

"Succinate buffer" refers a buffer that includes succinate ions. Examples of succinate buffer include succinic acid-sodium succinate, succinate histidine, succinic acid-potassium succinate, succinic acid-calcium succinate, and the like. The succinate buffer of the present disclosure is preferably succinic acid-sodium succinate.

"Acetate buffer" refers a buffer that includes acetate ions. Examples of the acetate buffer include acetic acid-sodium acetate, acetic acid histidine, acetic acid-potassium acetate, calcium acetate acetate, acetic acid-magnesium acetate, and the like. The preferred acetate buffer of the present disclosure is acetic acid-sodium acetate.

"Pharmaceutical composition" refers to a mixture comprising one or more of the compounds described herein or the physiologically/pharmaceutically acceptable salt thereof or the prodrug thereof with other chemical components. Said other chemical components are, for example, physiological/pharmaceutically acceptable carriers and excipients. The purpose of the pharmaceutical composition is to promote the administration into the organism, which facilitates the absorption of the active ingredient, thereby exerting biological activity.

The pharmaceutical composition of the present disclosure is capable of achieving a stable effect: the antibody in which can substantially retains its physical stability and/or chemical stability and/or biological activity after storage; preferably, the pharmaceutical composition substantially retains its physical stability, chemical stability and biological activity after storage. The shelf life is generally selected based on the predetermined shelf life of the pharmaceutical composition. There are currently a number of analytical techniques for measuring protein stability that measure stability after storage for a selected period of time at a selected temperature.

A stable antibody pharmaceutical preparation is one in which no significant change is observed in the following conditions: storage at a refrigerated temperature (2-8° C.) for at least 3 months, preferably 6 months, more preferably 1 year, and even more preferably up to 2 years. In addition, the stable liquid preparation includes a liquid preparation which exhibits a desired characteristic upon storage at a temperature including 25° C. and 40° C. for a period including 1 month, 3 months, and 6 months. Typical acceptable criteria for the stability are as follows: typically no more than about 10%, preferably no more than about 5% of antibody monomer is degraded, as assessed by SEC-HPLC. The pharmaceutical liquid preparation is colorless or clear to slightly opalescent white by visual analysis. The concentration, pH and osmolality of the preparation have no more than ±10% change. Typically, no more than 10%, preferably 5% of clipping is observed. Typically, no more than 10%, preferably 5% of aggregation is formed.

An antibody "retains its physical stability" in a pharmaceutical preparation if it shows no significant increase of aggregation, precipitation and/or denaturation upon visual examination of color and/or clarity, or as measured by UV light scattering, size exclusion chromatography (SEC) and dynamic light scattering (DLS). The changes of protein conformation can be evaluated by fluorescence spectroscopy (which determines the protein tertiary structure), and by FTIR spectroscopy (which determines the protein secondary structure).

An antibody "retains its chemical stability" in a pharmaceutical preparation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical preparation, if the biological activity of the antibody at a given time is within a predetermined range of the biological activity exhibited at the time the pharmaceutical preparation was prepared. The biological activity of an antibody can be determined, for example, by an antigen binding assay.

The three letter codes and single-letter codes for the amino acid residues used herein are described in *J. Biol. Chem.* 243, p. 3558 (1968).

The "antibody" as used in the present disclosure refers to an immunoglobulin, which is a tetra-peptide chain structure connected together by disulfide bonds between two identical heavy chains and two identical light chains. The difference in amino acid composition and order of the heavy chain constant region results in differences in immunoglobulin antigenicity. Accordingly, immunoglobulins can be classified into five classes, or called immunoglobulin isotypes, namely IgM, IgD, IgG, IgA, and IgE, the corresponding heavy chains of which are μ chain, δ chain, and γ chain, α chain and ε chain, respectively. According to its hinge region amino acid composition and the number and location of heavy chain disulfide bonds, the same isotype of Ig can be divided into different sub-classes, for example, IgG can be classified into IgG1, IgG2, IgG3, and IgG4. Light chains are classified as κ chain or λ chain according to the difference in the constant region. Each of the five classes of Ig can have a κ chain or a λ chain.

In the present disclosure, the antibody light chain of the present disclosure can further comprise a light chain constant region comprising a human or murine κ, λ chain or a variant thereof.

In the present disclosure, the antibody heavy chain of the present disclosure can further comprise a heavy chain constant region comprising human or murine IgG1, IgG2, IgG3, IgG4 or a variant thereof.

About 110 amino acids sequences adjacent to the N-terminus of the antibody heavy and light chains are highly variable, known as variable region (Fv region); the rest of amino acid sequences close to the C-terminus are relatively stable, known as constant regions. The variable region includes three hypervariable regions (HVR) and four relatively conserved framework regions (FR). The three hypervariable regions which determine the specificity of the antibody, are also known as the complementarity determining region (CDR). Each light chain variable region (LCVR) and each heavy chain variable region (HCVR) consists of three CDR regions and four FR regions, with sequentially order from the amino terminus to carboxyl terminus in the following order: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3. The number and position of CDR region amino acid residues in the LCVR and HCVR regions of the antibody or the antigen binding fragments herein comply with known Kabat numbering criteria (LCDR1-3, HCDE2-3), or comply with kabat and chothia numbering criteria (HCDR1).

The antibody of the present disclosure includes a murine antibody, a chimeric antibody and a humanized antibody, preferably a humanized antibody.

The term "murine antibody" in the present disclosure refers to a monoclonal antibody against human PD-L1 prepared according to the knowledge and skills of the field. During the preparation, a test subject was injected with PD-L1 antigen, and then the hybridoma expressing the antibody having the desired sequence or functional properties was separated. In a preferred embodiment of the present disclosure, the murine PD-L1 antibody or antigen-binding fragment thereof may further comprise a light chain constant region of murine κ, λ chain or a variant thereof, or may further comprise a heavy chain constant region of murine IgG1, IgG2, IgG3 or a variant thereof.

The term "chimeric antibody" is an antibody which is formed by fusing the variable region of a murine antibody with the constant region of a human antibody, and the chimeric antibody can alleviate the immune response that is induced by murine antibody. To construct a chimeric antibody, the hybridoma secreting a specific murine monoclonal antibody is first constructed, a variable region gene is cloned from the mouse hybridoma cells. Subsequently, a constant region gene of a human antibody is cloned as desired, the mouse variable region gene is ligated with the human constant region gene to form a chimeric gene which can be inserted into a human vector, and finally a chimeric antibody molecule is expressed in the eukaryotic or prokaryotic industrial system. In a preferred embodiment of the present disclosure, the light chain of the PD-L1 chimeric antibody further comprises the light chain constant regions of human κ, λ chain, or a variant thereof. The heavy chain of the PD-L1 chimeric antibody further comprises the heavy chain constant regions of human IgG1, IgG2, IgG3, or IgG4, or a variant thereof. The constant region of a human antibody can be selected from the heavy chain constant region of human IgG1, IgG2, IgG3 or IgG4 or a variant thereof, preferably comprising the heavy chain constant region of human IgG2 or IgG4, or IgG4 without ADCC (antibody-dependent cell-mediated cytotoxicity) after amino acid mutation.

The term "humanized antibody", also known as CDR-grafted antibody, refers to an antibody generated by grafting murine CDR sequences into a variable region framework of a human antibody, namely, an antibody produced from different type of human germline antibody framework sequence. A humanized antibody overcomes the disadvantage of the strong antibody response induced by the chimeric antibody, which carries a large amount of murine protein components. Such framework sequences can be obtained from a public DNA database covering germline antibody gene sequences or published references. For example, germline DNA sequences of human heavy and light chain variable region genes can be found in "VBase" human germline sequence database (available on web www.mrccpe.com.ac.uk/vbase), as well as can be found in Kabat, E A, et al, 1991 *Sequences of Proteins of Immunological Interest,* 5th Ed. To avoid the decrease in activity while the decrease of immunogenicity, the framework sequences in the variable region of the human antibody are subjected to minimal reverse mutations or back mutations to maintain the activity. The humanized antibody of the present disclosure also comprises a humanized antibody to which CDR affinity maturation is performed by phage display.

"Antigen-binding fragment" in the present disclosure refers to a Fab fragment, a Fab' fragment, or a F(ab')2 fragment having antigen-binding activity, as well as a Fv or scFv fragment binding to human PD-L1; it comprises one or more CDR regions of antibodies described in the present disclosure, selected from the group consisting of SEQ ID NO: 1 to SEQ ID NO: 12. A Fv fragment comprises heavy chain variable region and light chain variable region, without constant region, and it is a minimal antibody fragment possessing all antigen-binding sites. Generally, a Fv antibody further comprises a polypeptide linker between the VH and VL domains, and is capable of forming a structure necessary for antigen binding. Also, different linkers can be used to connect the variable regions of two antibodies to form a polypeptide chain, referred to as a single chain antibody or single chain Fv (scFv). The term "binding to PD-L1" in the present disclosure means that it is capable of interacting with human PD-L1. The term "antigen-binding sites" in the present disclosure refers to the discontinuous three-dimensional sites on the antigen, recognized by the antibody or the antigen-binding fragment of the present disclosure.

Methods for producing and purifying antibodies and antigen-binding fragments are well known in the art and can be found, for example, in *Antibody Experimental Technology Guide of Cold Spring Harbor*, Chapters 5-8 and 15. For example, a mouse can be immunized with human PD-L1 or a fragment thereof, and the obtained antibody can be renatured, purified, and subjected to amino acid sequencing by a conventional method. The antigen-binding fragment can also be prepared by a conventional method. The antibody or the antigen-binding fragments of the present disclosure is genetically engineered to introduce one or more human framework regions (FRs) to a non-human derived CDR region. Human FR germline sequences can be obtained from ImMunoGeneTics (IMGT) via their website http://imgt.cines.fr, or from *The Immunoglobulin FactsBook*, 20011SBN012441351.

The engineered antibody or antigen-binding fragments of the present disclosure can be prepared and purified by conventional methods. For example, cDNA sequences encoding a heavy chain and a light chain can be cloned and recombined into a GS expression vector. The recombined immunoglobulin expression vector can then be stably transfected into CHO cells. As a more recommended method well known in the art, mammalian expression systems will result in glycosylation of antibodies, typically at the highly conserved N-terminus in the Fc region. Stable clones can be obtained through expression of an antibody specifically binding to human PD-L1. Positive clones can be expanded in serum-free culture medium for antibody production in bioreactors. Culture medium, into which an antibody has been secreted, can be purified by conventional techniques. For example, the medium can be conveniently applied by a Protein A or G Sepharose FF column that has been equilibrated with adjusted buffer. The column is washed to remove nonspecific binding components. The bound antibody is eluted by pH gradient and antibody fragments are detected by SDS-PAGE, and then pooled. The antibody can be filtered and concentrated using common techniques. Soluble aggregate and multimers can be effectively removed by common techniques, including size exclusion or ion exchange. The obtained product can be immediately cryopreserved, for example at −70° C., or can be lyophilized.

"Conservative modifications" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skilled in this art recognize that, in general, single amino acid substitutions in non-essential regions of a polypeptide does not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity.

"Identity" refers to sequence similarity between two polynucleotide sequences or between two polypeptides. When a position in both of the two compared sequences is occupied by the same base or amino acid monomer subunit, e.g., if a position in each of two DNA molecules is occupied by adenine, the molecules are identical at that position. The percent identity between the two sequences is a function of the number of matched or consistent positions shared by the two sequences divided by the number of compared positions ×100. For example, in the optimal alignment of sequences, if there are 6 matches or consistencies in 10 positions of the two sequences, then the two sequences have 60% identity. In general, comparisons are made when the two sequences are aligned to obtain the highest percent identity.

"Administration" and "treatment," when applying to an animal, human, experimental subject, cell, tissue, organ, or biological fluid, refer to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also means in vitro and ex vivo treatments, e.g., of a cell, by a reagent, diagnostic, binding compound, or by another cell. "Treatment", as it applies to a human, veterinary, or a research subject, refers to therapeutic treatment, prophylactic or preventative measures, research and diagnostic applications.

"Treat" means to administer a therapeutic agent, such as a composition comprising any of the binding compounds of the present disclosure, internally or externally to a patient having one or more disease symptoms for which the agent has known therapeutic activity. Typically, the agent is administered in an amount effective to alleviate one or more disease symptoms in the treated patient or population, so as to induce the regression of or inhibit the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject can vary depending on factors such as the condition being treated, the general health of the patient, the route and dose of administration and the severity of side effects. An effective amount can be the maximal dose or dosing protocol that avoids significant side effects or toxic effects.

"Tm value" refers to the thermal denaturation midpoint of the protein, namely, the temperature at which half of the protein is unfolded and the spatial structure of the protein is destroyed. Therefore, the higher the Tm value is, the higher the thermal stability of the protein will be.

The disclosure is further described with the following embodiments, which are not intended to limit the scope of the invention. The experimental methods in the embodiments of the present disclosure which do not specify the specific conditions are usually carried out according to conventional conditions or according to the conditions recommended by the manufacturer of the raw material or the commodity. Reagents without specific source are routine reagents commercially available.

In the embodiments, Agilent-HPLC 1260 high pressure liquid chromatograph (Waters Xbridge® BEH 200Å SEC 3.5 μm 7.8×300 mm column and Thermo ProPac™ WCX-10 BioLC™, 250×4 mm column) was used to measure SE-HPLC and IEC-HPLC. Beckman PA800 plus capillary electrophoresis apparatus (SDS-Gel MW Analysis Kit) was used to measure reduced CE-SDS and non-reduced CE-SDS. GE MicroCal VP-Capillary DSC differential scanning calorimeter was used to measure the thermal denaturation temperature midpoint of the protein (Tm). Malvern Zetasizer Nano ZS nanoparticle size potentiometer was used to measure DLS (Dynamic Light Scattering) average particle size.

Embodiment 1: Preparation of the PD-L1 Antibody (1) Preparation of the PD-L1 Antigen and the Protein Used for Detection The human PD-L1 full-length gene (Sino Biological Inc., HG10084-M) of UniProt Programmed Cell Death1 Ligand1 (PD-L1) isoform1 (SEQ ID NO: 19) was used as a template for the PD-L1 of the present disclosure. A gene sequence encoding the antigen of the present disclosure and the protein used for detection was obtained, optionally recombined with the heavy chain Fc fragment of antibody (such as human IgG1), cloned into a pTT5 vector (Biovector, Cat #: 102762) or a pTargeT vector (promega, A1410), subjected to transient expression in 293F cells (Invitrogen, R79007) or stable expression of CHO-S cells (Invitrogen, k9000-20), and purified to obtain the antigen and the detection protein of the present disclosure. The human PD-1 gene was purchased from ORIGENE, Art. No. SC117011, NCBI Reference Sequence: NM_005018.1.

1. Human PD-L1 Full-Length Amino Acid Sequence

SEQ ID NO: 19
MRIFAVFIFM TYWHLLNAFT VTVPKDLYVV EYGSNMTIEC

KFPVEKQLDL AALIVYWEME DKNIIQFVHG EEDLKVQHSS

YRQRARLLDK QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR *LRKGRMMDVK KCGIQDTNSK*

*KQSDTHLEET*

Note: The part with double underline is the signal peptide (1-18); the part with single underline is the extracellular domain (19-238) of PD-L1, wherein 19-127 is Ig-like V-type Domain, 133-225 is Ig-like C2-type Domain; the part with dotted underline is the transmembrane domain (239-259); and the italicized part is the cytoplasmic domain (260-290).

2. Immunogen: PD-L1 with his and PADRE tags: PD-L1 (Extra Cellular Domain, abbr. ECD)-PADRE-His6

SEQ ID NO: 20
FT VTVPKDLYVV EYGSNMTIEC KFPVEKQLDL AALIVYWEME

DKNIIQFVHG EEDLKVQHSS YRQRARLLKD QLSLGNAALQ

ITDVKLQDAG VYRCMISYGG ADYKRITVKV NAPYNKINQR

ILVVDPVTSE HELTCQAEGY PKAEVIWTSS DHQVLSGKTT

TTNSKREEKL FNVTSTLRIN TTTNEIFYCT FRRLDPEENH

TAELVIPELP LAHPPNERGS GAKFVAAWTLKAAA*HHHHHH*

Note: The part with single underline is the extracellular domain of PD-L1; the part with dotted underline is the PADRE label; and the italicized part is the His6-tag label.

3. PD-L1 with FLAG and HIS tags was obtained; PD-L1 (ECD)-Flag-His6 was used to test the performance of the antibodies of the present disclosure.

SEQ ID NO: 21
FT VTVPKDLYVV EYGSNMTIEC KFPVEKQLDL AALIVYWEME

DKNIIQFVHG EEDLKVQHSS YRQRARLLKD QLSLGNAALQ

ITDVKLQDAG VYRCMISYGG ADYKRITVKV NAPYNKINQR

ILVVDPVTSE HELTCQAEGY PKAEVIWTSS DHQVLSGKTT

TTNSKREEKL FNVTSTLRIN TTTNEIFYCT FRRLDPEENH

TAELVIPELP LAHPPNERDY KDDDDK*HHHH HH*

Note: The part with single underline is the extracellular domain of PD-L1; the part with dotted underline is the FLAG-Tag label; and the italicized part is the His6-tag label.

4. The Fc fusion protein of PD-L1: PD-L1 (ECD)-Fc was used as the immunological antigen or detection reagent of the present disclosure.

VKL-PD-L1 (ECD)-Fc(human IgG1)
SEQ ID NO: 22
FT VTVPKDLYVV EYGSNMTIEC KFPVEKQLDL AALIVYWEME

DKNIIQFVHG EEDLKVQHSS YRQRARLLKD QLSLGNAALQ

ITDVKLQDAG FTVTVPKDLYVVEYGSNMTIECKFPVEKQLDLAALIVYW

EMEDKNIIQFVHGEEDLKVQHSSYRQRARLLKDQLSLGNAALQITDVKLQ

DAGVYRCMISYGGADYKRITVKVNAPYNKINQRILVVDPVTSEHELTCQA

EGYPKAEVIWTSSDHQVLSGKTTTTNSKREEKLFNVTSTLRINTTTNEIF

YCTFRRLDPEENHTAELVIPELPLAHPPNER*DKTHTCPPCPAPELLGGPS*

*VFLFPPKPKDTLMISRTPEVTCVVVDVSHEDPEVKFNWYVDGVEVHNAKT*

*KPREEQYNSTYRVVSVLTVLHQDWLNGKEYKCKVSNKALPAPIEKTISKA*

-continued

KGQPREPQVYTLPPSREEMTKNQVSLTCLVKGFYPSDIAVEWESNGQPEN

NYKTTPPVLDSGSFFLYSKLTVDKSRWQQGNVFSCSVMHEALHNHYTQK

SLSLSPGK

Note: The part with single underline is the extracellular domain of PD-L1; and the italicized part is the part of human IgG1 Fc.

5. The Fc fusion protein of PD-L1: PD-L1 (ECD)-Fc was used to test the performance of the antibodies of the present disclosure.

SEQ ID NO: 23
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLV

EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Note: The part with single underline is the extracellular domain (ECD) of PD-L1; and the italicized part is the part of hFc (human IgG1).

(2) Purification of PD-L1, PD-1 Recombinant Protein as Well as Hybridoma Antibody and Recombinant Antibody 1. Purification of "PD-L1 with his and PADRE Tag": PD-L1 (ECD)-PADRE-His6 (SEQ ID NO: 20) Recombinant Protein The cell expression supernatant sample was centrifuged at high speed to remove impurities, and the buffer was displaced with PBS, followed by addition of imidazole to a final concentration of 5 mM. The nickel column was equilibrated with PBS solution containing 5 mM imidazole and washed with 2-5 column volumes. The supernatant sample was loaded on a Ni column (GE, 17-5318-01). The column was washed with PBS containing 5 mM imidazole until the A280 reading dropped to baseline. The column was washed with PBS plus 10 mM imidazole to remove the non-specific binding impure protein, and the effluent was collected. The target protein was eluted with PBS containing 300 mM imidazole, and the elution peak was collected. The collected eluent was concentrated and further purified by gel chromatography Superdex 200 (GE) with PBS as the mobile phase. The polymer peaks were discarded and the elution peaks were collected. The obtained protein was confirmed by the identification of electrophoresis, peptide mapping (Agilent, 6530 Q-TOF) and LC-MS (Agilent, 6530 Q-TOF), and aliquoted for subsequent use. PD-L1 with His and PADRE tag: PD-L1 (ECD)-PADRE-His6 (SEQ ID NO: 2) was obtained and used as an immunogen for the antibody of the present disclosure.

2. Purification of PD-L1 (ECD)-Flag-His6 (SEQ ID NO: 21) Recombinant Protein with His Tag and Flag Tag The sample was centrifuged at high speed to remove impurities and concentrated to a desired volume. The protein peak eluted from the IMAC column as above was loaded onto a 0.5×PBS equilibrated flag affinity column (Sigma, A2220) and washed with 2-5 column volumes. The cell expression supernatant sample was loaded on the column after removing the impurities. The column was washed with 0.5×PBS until the A280 reading dropped to baseline. The column was washed with PBS containing 0.3 M NaCl, and the impure protein was eluted and collected. The target protein was eluted with 0.1 M acetic acid (pH 3.5-4.0) and collected, followed by adjusting pH to neutral. The collected elution was concentrated and further purified by gel chromatography Superdex 200 (GE) with PBS as the mobile phase. The polymer peaks were discarded and the elution peaks were collected. The collected sample was confirmed by the identification of electrophoresis, peptide mapping and LC-MS, and aliquoted for subsequent use. PD-L1 with His tag and Flag tag, i.e. PD-L1 (ECD)-Flag-His6 (SEQ ID NO: 3) was obtained for testing the performance of the antibody of the present disclosure.

3. Purification of Fc Fusion Protein of PD-L1 and PD-1

The cell expression supernatant sample was centrifuged at high speed to remove impurities, concentrated to a desired volume, and loaded onto a Protein A column (GE, 17-5438-01). The column was washed with PBS until the A280 reading drops to baseline. The protein of interest was eluted with 100 mM sodium acetate at pH 3.0. The protein neutralized by 1M TrisHCl was further purified by PBS-equilibrated gel chromatography Superdex 200 (GE). The polymer peaks were discarded and the elution peaks were collected and aliquoted for subsequent use. This method was used to purify PD-L1 (ECD)-Fc (SEQ ID NO: 4) and PD-1 (ECD)-Fc (SEQ ID NO: 5). PD-L1 (ECD)-Fc can be used as the immunizing antigen or the detecting reagent of the present disclosure, and PD-1 (ECD)-Fc can be used for testing the performance of the antibody of the present disclosure.

(3) Preparation of Anti-Human PD-L1 Hybridoma Monoclonal Antibody

1. Immunization

Anti-human PD-L1 monoclonal antibody was produced from immunizing a mouse, wherein SJL white mice, female, 6 weeks old (Beijing Vital River Laboratory Animal Technology Co., Ltd., animal production license number: SCXK (Beijing) 2012-0001) were used. Feeding environment: SPF level. After the mice were purchased, the mice were reared under the laboratory environment (12/12 hours light/dark cycle adjustment, temperature 20-25° C.; humidity 40-60%) for 1 week. Mice that have adapted to the environment were immunized in two schemes (Scheme A and Scheme B), 6-10 per group. The immunizing antigen was PD-L1 with His and PADRE tag: PD-L1 (ECD)-PADRE-His6 (SEQ ID NO: 20).

In Scheme A, Freund's adjuvant (sigma Lot Num: F5881/F5506) was used for emulsification: complete Freund's adjuvant (CFA) was used for the primary immunization, and incomplete Freund's incomplete adjuvant (IFA) was used for the rest boost immunization. The ratio of the antigen to the adjuvant was 1:1, 100 µg/mouse (primary immunization), 50 µg/mouse (boost immunization). The emulsified antigen was intraperitoneally injected at 100 µg/mouse on Day 0, and injected once every two weeks after the primary immunization for a total of 6-8 weeks.

In Scheme B, Titermax (sigma Lot Num: T2684) and Alum (Thremo Lot Num: 77161) were used for cross-immunization. The ratio of the antigen to the adjuvant (titermax) was 1:1, and the ratio of the antigen to the adjuvant (Alum) was 3:1, 10-20 µg/per mouse (primary immunization), and 5 µg/per mouse (boost immunization). The emulsified antigen was intraperitoneally injected at 20/10 µg/mouse on Day 0, and injected once a week after the primary immunization. Titermax was used with Alum interchangeably for 6-11 weeks. After four weeks of immunization, the antigen was administered via back or intraperitoneal injection based on the condition of back lump and the abdominal swelling.

2. Cell Fusion

The mice with high serum antibody titer tending to reach a plateau were selected for splenocytes fusion. A shock immunization was performed by intraperitoneal injection 72 hours prior to splenocyte fusion. The hybridoma cells were obtained by fusing spleen lymphocytes with myeloma cell Sp2/0 cells (ATCC® CRL8287™) via an optimized PEG-mediated fusion procedure. The hybridoma cells were resuspended in HAT complete medium (RPMI-1640 medium containing 20% FBS, 1×HAT and 1×OPI) and aliquoted into 96-well cell culture plates (1×10⁵/150 μL/well), followed by incubation at 37° C. under 5% $CO_2$. On the 5$^{th}$ day after fusion, HAT complete medium was added, 50 μL/well, and incubated at 37° C. under 5% $CO_2$. From the 7$^{th}$ day to the 8th day after the fusion, according to the cell growth density, the whole medium was changed by HT complete medium (RPMI-1640 medium containing 20% FBS, 1×HT and 1×OPI) at 200 μL/well, and incubated at 37° C. under 5% $CO_2$.

3. Hybridoma Cell Screening

On the 10th day to the 11th day after fusion, ELISA method of PD-L1 binding was performed according to the cell growth density. The positive well cells detected in ELISA were subjected to blocking ELISA of PD-L1/PD-1 binding. The medium in the positive wells was changed, and the positive cells were expanded into 24-well plates according to cell density. The cells transferred into the 24-well plate was subjected to retesting and then subjected to cell preservation and initial subcloning. The positive one screened after the initial subcloning was subjected to cell preservation, followed by the second subcloning. The positive one screened after the initial subcloning was subjected to cell preservation, followed by protein expression. The hybridoma cells that blocked the binding of PD-L1 and PD-1 were obtained by multiple fusions.

Hybridoma clone cells 1 and 2 were screened by blocking assay and binding assay. The antibodies were further prepared by ascites method or by serum-free cell culture method, and the antibodies were purified according to the purification embodiments for use in the test embodiments.

The variable region sequences of the murine antibody were obtained by sequencing, wherein the CDR variable region sequences of the hybridoma clones were shown in Table 1 below:

TABLE 1

| Heavy chain | Light chain |
|---|---|
| 1 HCDR1 NDYWX₁<br>SEQ ID NO: 1 | LCDR1 KSSQSLFYX₂SNQKX₃SLA<br>SEQ ID NO: 4 |
| HCDR2 YISYTGSTYYNPSLKS<br>SEQ ID NO: 2 | LCDR2 GASTRES<br>SEQ ID NO: 5 |
| HCDR3 SGGWLAPFDY<br>SEQ ID NO: 3 | LCDR3 QQYYGYPYT<br>SEQ ID NO: 6 |
| 2 HCDR1 SYWMH<br>SEQ ID NO: 7 | LCDR1 RASESVSIHGTHLMH<br>SEQ ID NO: 10 |
| HCDR2 RIX₄PNSGX₅TSYNEKFKN<br>SEQ ID NO: 8 | LCDR2 AASNLES<br>SEQ ID NO: 11 |
| HCDR3 GGSSYDYFDY<br>SEQ ID NO: 9 | LCDR3 QQSFEDPLT<br>SEQ ID NO: 12 |

Wherein $X_1$ is selected from N or T, $X_2$ is selected from R or H, $X_3$ is selected from N or H, $X_4$ is selected from H or G, and $X_5$ is selected from G or F.

(4) Humanization of Anti-Human PD-L1 Hybridoma Monoclonal Antibody

The germline genes with high homologous in heavy and light chain variable region were selected as templates by aligning with the human antibody heavy light chain variable region germline gene database of IMGT and MOE software. The CDRs of murine antibody 1 and 2 were transplanted into the corresponding humanized template, and affinity-matured to form a variable region sequence of FR1-CDR1-FR2-CDR2-FR3-CDR3-FR4.

The humanized light chain template of murine antibody 1 is IGKV4-1*01 and hjk4.1, the humanized heavy chain template is IGHV4-30-4*01 and hjh2, and the humanized variable region sequences are as follows:

>1 hVH- CDR graft
SEQ ID NO: 24
QVQLQESGPGLVKPSQTLSLTCTVSGGSIS<u>NDYWN</u>WIRQHPGKGLEWIG<u>Y</u>

<u>ISYTGSTYYNPSLKS</u>RVTISVDTSKNQFSLKLSSVTAADTAVYYCARS<u>GG</u>

<u>WLAPFDY</u>WGRGTLVTVSS

>1 hVL CDR graft
SEQ ID NO: 25
DIVMTQSPDSLAVSLGERATINC<u>KSSQSLFYRSNQKNSLA</u>WYQQKPGQPP KLLIY<u>GASTRES</u>GVPDRFSGSGSGTDFTLTISSLQAEDVAVYYC<u>QQYYGY</u>

<u>PYT</u>FGGGTKVEIK

The humanized light chain template of murine antibody 2 is IGKV7-3*01 and hjk2.1, the humanized heavy chain template is IGHV1-46*01 and hjh6.1, and the sequence of humanized variable region is as follows:

>2- hVH.1
SEQ ID NO: 26
QVQLVQSGAEVKKPGASVKVSCKASGYTFT<u>SYWMH</u>WVRQAPGQGLEWMG<u>R</u>

<u>IHPNSGGTSYNEKFKN</u>RVTMTRDTSTSTVYMELSSLRSEDTAVYYCAR<u>GG</u>

<u>SSYDYFDY</u>WGQGTTVTVSS

>2-hVL.1
SEQ ID NO: 27
DIVLTQSPASLAVSPGQRATITC<u>RASESVSIHGTHLMH</u>WYQQKPGQPPKL

LIY<u>AASNLES</u>GVPARFSGSGSGTDFTLTINPVEANDTANYYC<u>QQSFEDPL</u>

<u>T</u>FGQGTKLEIK

Note: The order is FR1-CDR1-FR2-CDR2-FR3-CDR3-FR4, wherein the italicized part is FR sequence and the part with underline is CDR sequence.

(5) Humanized Clone Construction

The primers were designed to construct the VH/VK gene fragment of each humanized antibody, and then homologously recombined with the expression vector pHr (with signal peptide and constant region gene (CH1-FC/CL) fragment) to construct the full-length antibody expression vector VH-CH1-FC-pHr/VK-CL-pHr.

1. Primer design: The online software DNAWorks (v3.2.2) (http://helixweb.nih.gov/dnaworks/) was used to design a plurality of primers to synthesize VH/VK containing gene fragments required for recombination: 5'-30 bp signal peptide+VH/VK+30 bp CH1/CL-3'. Primer design principle: If there are different amino acids between Target gene 2 and Target gene 1, then another primer comprising mutation site was design, as shown in FIG. 1.

2. Fragment splicing: According to the operating instructions of TaKaRa Primer STAR GXL DNA polymerase, the VH/VK containing gene fragments required for recombination was obtained by two steps PCR amplification using a plurality of primers designed above.

3. Construction and Enzymatic Digestion of Expression Vector pHr (with Signal Peptide and Constant Region Gene (CH1-FC/CL) Fragment)

Figure 2:
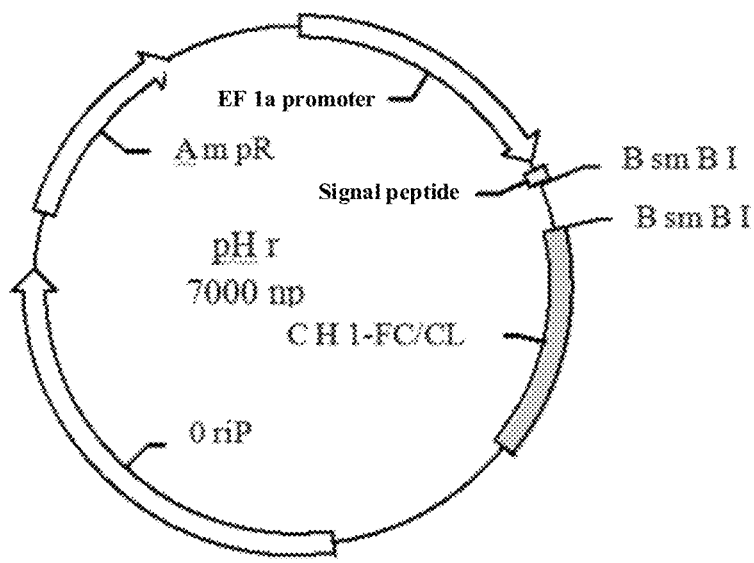
FIG. 2: The schematic diagram of vector construction during humanized clone construction.

The expression vector pHr (with signal peptide and constant region gene (CH1-FC/CL) fragment) was constructed by using some special restriction endonucleases with special design of which the recognition sequence was different from the restriction sites, such as BsmBI. The schematic diagram of construction was shown in FIG. 2. The vector was digested with BsmBI, and the gel was extracted for use.

4. Recombinant Construction of Expression Vector VH-CH1-FC-pHr/VK-CL-pHr

VH/VK containing gene fragments required for recombination and BsmBI digested and recovered expression vector pHr (with signal peptide and constant region gene (CH1-FC/CL) fragment) were added to DHSH competent cells in a molar ratio of 3:1, maintained in 0° C. ice bath for 30 minutes, subjected to heat shock at 42° C. for 90 seconds, followed by addition of 5-fold volumes of LB medium, incubated at 37° C. for 45 minutes, and spread on LB-Amp plate and incubated at 37° C. overnight. The single clone was selected and sent for sequencing to obtain the target clone.

(6) Affinity Maturation of Anti-PD-L1 Humanized Antibody

1. Construction of Phagemid Vectors of Humanized PD-L1 Antibodies 1 and 2

Humanized PD-L1 antibodies 1 and 2 were constructed into phagemid vectors in scFv mode (VH-(GGGGS)$_3$-VL), respectively, as wild-type sequences (i.e., it's an original or starting sequence corresponding to mutant sequences screened for affinity maturation). VH, (GGGGS)$_3$ linker and VL were assembled by over-lap PCR and ligated into phagemid vector via NcoI and NotI restriction recognition sites.

2. Construction of Phage Display Library

The constructed wild-type scFv was used as a template and codon-based primers was used. In the primer synthesis process, each codon in the mutation region had 50% wild-type codon and 50% NNK (reverse primer was MNN), which introduced mutations to all CDR regions to construct a mutant library. The PCR fragment was digested with NcoI and NotI, ligated into a phagemid vector, and finally electrically transformed into *E. coli* TG1. An independent library was constructed by each codon-based primer, in which antibody 1 was divided into 7 libraries and antibody 2 was divided into 8 libraries.

3. Library Panning

After the library was rescued and packaged for phage particles for panning, the biotinylated human PD-L1 (ECD) antigen and streptavidin magnetic beads were used for liquid phase panning, and the antigen concentration after each round of screening was decreased compared to the previous round. After three rounds of panning, 250 clones were selected from antibody 1 and antibody 2 and subjected to phage ELISA to detect binding activity, respectively, followed by sequencing the positive clones.

4. Surface Plasmon Resonance (SPR) Detection of Affinity

After sequencing the clones, the redundant sequences were removed, and the non-redundant sequences were converted into full-length IG (γ1, κ) for mammalian cell expression. The full-length IG after affinity purification was subjected to affinity detection using a BIAcore™ X-100 instrument (GE Life Sciences).

The variable region sequences of the humanized antibody 2 after affinity maturation are shown as follows:
Heavy Chain Variable Region:

SEQ ID NO: 13
QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSS

Wherein, X$_4$ of CDR2 is G, X$_5$ is F.
Light Chain Variable Region:

SEQ ID NO: 14
DIVLTQSPASLAVSPGQRATITCRASESVSIHGTHLMHWYQQKPGQPPKL

LIYAASNLESGVPARFSGSGSGTDFTLTINPVEAEDTANYYCQQSFEDPL

TFGQGTKLEIK

Note: The italicized part in the sequence is FR sequence; the part with underline is CDR sequence; and the site with double underline is the site obtained after affinity maturation screening.

The variable region sequences of humanized antibody 1 after affinity maturation are as follows:
Heavy Chain Variable Region

SEQ ID NO: 28
QVQLQESGPGLVKPSQTLSLTCTVSGGSISNDYWTWIRQHPGKGLEYIGY

ISYTGSTYYNPSLKSRVTISRDTSKNQFSLKLSSVTAADTAVYYCARSGG

WLAPFDYWGRGTLVTVSS

Wherein, X$_4$ of CDR1 is T.
Light Chain Variable Region:

SEQ ID NO: 29
DIVMTQSPDSLAVSLGERATINCKSSQSLFYHSNQKHSLAWYQQKPGQPP

KLLIYGASTRESGVPDRFSGSGSGTDFTLTISSLQAEDVAVYYCQQYYGY

PYTFGGGTKVEIK

Wherein, CDR1 X$_2$ is H and X$_3$ is H.

The clone obtained by affinity maturation was converted to the IgG4 type, and IgG4 of which the core hinge region contain the S228P mutation was selected to obtain an antibody without ADCC and CDC, wherein the antibody obtained from the antibody 2 was named HRP00052.

The last three nucleotides "TGA" of the following gene sequences SEQ ID NO: 16 and 18 are stop codons and do not encode any amino acids.
Heavy Chain Sequence of HRP00052 Antibody

SEQ ID NO: 15
QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

-continued

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

Heavy Chain Sequence Encoding Gene Sequence of HRP00052 Antibody

SEQ ID NO: 16
CAGGTGCAACTGGTGCAGAGCGGTGCCGAGGTGAAGAAGCCTGGCGCAAG

CGTGAAAGTGAGCTGCAAGGCCAGCGGCTACACCTTCACCAGCTACTGGA

TGCACTGGGTGAGGCAGGCCCCTGGACAGGGCCTGGAGTGGATGGGCAGG

ATCGGGCCCAACAGTGGTTTCACTAGCTACAATGAAAAGTTCAAGAACAG

GGTAACCATGACCAGGGACACCTCCACCAGCACAGTGTATATGGAGCTGA

GCAGCCTGAGGAGCGAGGACACCGCCGTGTACTACTGTGCCAGAGGCGGC

AGCAGCTACGACTACTTCGACTATTGGGGCCAGGGCACCACCGTGACCGT

GAGCAGTGCTTCCACCAAGGGCCCATCGGTCTTCCCCCTGGCGCCCTGCT

CCAGGAGCACCTCCGAGAGCACAGCCGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACGAAGACCTAC

ACCTGCAACGTAGATCACAAGCCCAGCAACACCAAGGTGGACAAGAGAGT

TGAGTCCAAATATGGTCCCCCATGCCCACCATGCCCAGCACCTGAGGCTG

CTGGGGGACCATCAGTCTTCCTGTTCCCCCCAAAACCCAAGGACACTCTC

ATGATCTCCCGGACCCCTGAGGTCACGTGCGTGGTGGTGGACGTGAGCCA

GGAAGACCCCGAGGTCCAGTTCAACTGGTACGTGGATGGCGTGGAGGTGC

ATAATGCCAAGACAAAGCCGCGGGAGGAGCAGTTCAACAGCACGTACCGT

GTGGTCAGCGTCCTCACCGTCCTGCACCAGGACTGGCTGAACGGCAAGGA

GTACAAGTGCAAGGTCTCCAACAAAGGCCTCCCGTCCTCCATCGAGAAAA

CCATCTCCAAAGCCAAAGGGCAGCCCCGAGAGCCACAGGTGTACACCCTG

CCCCCATCCCAGGAGGAGATGACCAAGAACCAGGTCAGCCTGACCTGCCT

GGTCAAAGGCTTCTACCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAGGCTCACCGTGGACAAGAGCAGGTGGCA

GGAGGGGAATGTCTTCTCATGCTCCGTGATGCATGAGGCTCTGCACAACC

ACTACACACAGAAGAGCCTCTCCCTGTCTCTGGGTAAATGA

Light Chain Sequence of HRP00052 Antibody

SEQ ID NO: 17
DIVLTQSPASLAVSPGQRATITCRASESVSIHGTHLMHWYQQKPGQPPKL

LIYAASNLESGVPARFSGSGSGTDFTLTINPVEAEDTANYYCQQSFEDPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Light Chain Sequence Encoding Gene Sequence of HRP00052 Antibody

SEQ ID NO: 18
GACATCGTGCTGACCCAGAGTCCCGCCTCACTTGCCGTGAGCCCCGGTCA

GAGGGCCACCATCACCTGTAGGGCCAGCGAGAGCGTGAGCATCCACGGCA

CCCACCTGATGCACTGGTATCAACAGAAACCCGGCCAGCCCCCCAAACTG

CTGATCTACGCCGCCAGCAACCTGGAGAGCGGCGTGCCCGCCAGGTTCAG

CGGCTCCGGCAGCGGCACCGACTTCACCCTCACTATCAACCCCGTGGAGG

CCGAGGACACCGCCAACTACTACTGCCAGCAGAGCTTCGAGGACCCCCTG

ACCTTCGGCCAGGGCACCAAGCTGGAGATCAAGCGTACGGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTGA

Note: The part with underline is the variable region sequence of the antibody heavy or light chain, or the nucleotide sequence encoding the same; the unlined part is the antibody constant region sequence and the corresponding coding nucleotide sequence thereof.

An expression plasmid for expressing the PD-L1 antibody HRP00052 was constructed. The nucleotide sequences encoding the heavy and light chains, and the corresponding promoter thereof and the polyadenylation signal sequences thereof were confirmed by DNA sequence analysis. The expression vector was transfected into a CHO cell line. Clones expressing the antibody were selected based on growth and production stability, followed by preparation of a master seed bank, which was used to prepare antibodies and generate a master cell bank thereafter.

The cells from the master cell bank were propagated in shake flasks, culture bags and seed bioreactors, and the obtained seed cells were used to produce antibody products by a bioreactor. The obtained antibody was subjected to further purification by protein A affinity chromatography, cation exchange chromatography and anion exchange chromatography, as well as low pH virus inactivation and filtration steps to remove the virus. The specific purification steps were as follows. The cell expression supernatant sample was loaded onto a PBS buffer equilibrated Protein A column (Merck, 175118824). The column was washed with PBS until the A280 reading was lowered to the baseline, and then washed with PB buffer to remove the impure protein. The target protein was eluted with 50 mM sodium citrate at pH 3.5 and the eluted peak was collected. Purification was neutralized with 1M Tris and loaded onto an anion chromatography column (GE, 17-5316-10) equilibrated with PB buffer, and the flow-through peak was collected and adjusted to pH 5.0 with 1 M citric acid. After anion chromatography, the protein was further purified on a cation chromatography column (Merck, 1.168882) equilibrated with a citrate buffer (pH 5.0). The target protein was eluted with a citrate buffer (pH 5.0) containing 0.18 M sodium chloride, and the eluted peak was collected and aliquoted for subsequent use.

Embodiment 2

The experiments were designed based on the buffer system, buffer concentration, pH value, saccharide type and saccharide concentration of the PD-L1 preparation (1 mg/mL). Tm value of the sample was determined by DSC technique to initially screen the formulation of the preparation.

The buffer system, buffer concentration, pH value, saccharide type and saccharide concentration were used as the factors, and the Tm value was used as the response value to design the test and generate a design table. The Tm value was determined according to the experimental groups of the design table.

TABLE 2

DSC results with Tm value response

| | Buffer system | Buffer concentration (mM) | pH | Saccharide type | Saccharide concentration (%) | Tm |
|---|---|---|---|---|---|---|
| 1 | Succinic acid-sodium succinate | 10 | 5 | Trehalose | 3 | 83.35 |
| 2 | Succinic acid-sodium succinate | 10 | 5.3 | Sucrose | 6 | 84.13 |
| 3 | Succinic acid-sodium succinate | 20 | 5.6 | Sucrose | 6 | 83.89 |
| 4 | Succinic acid-sodium succinate | 30 | 5 | Sucrose | 6 | 83.06 |
| 5 | Succinic acid-sodium succinate | 30 | 5.6 | Trehalose | 3 | 83.49 |
| 6 | Acetic acid-sodium acetate | 10 | 5 | Sucrose | 9 | 84.57 |
| 7 | Acetic acid-sodium acetate | 10 | 5.6 | Sucrose | 3 | 84.15 |
| 8 | Acetic acid-sodium acetate | 30 | 5 | Trehalose | 6 | 84.03 |
| 9 | Acetic acid-sodium acetate | 30 | 5.6 | Sucrose | 9 | 84.51 |
| 10 | Histidine-histidine hydrochloride | 10 | 5 | Sucrose | 6 | 82.41 |
| 11 | Histidine-histidine hydrochloride | 10 | 5.6 | Trehalose | 9 | 83.96 |
| 12 | Histidine-histidine hydrochloride | 20 | 5.3 | Trehalose | 3 | 81.92 |
| 13 | Histidine-histidine hydrochloride | 30 | 5 | Trehalose | 9 | 80.85 |
| 14 | Histidine-histidine hydrochloride | 30 | 5.6 | Sucrose | 6 | 83.03 |
| 15 | Citric acid-disodium phosphate | 10 | 5 | Trehalose | 6 | 83.41 |
| 16 | Citric acid-disodium phosphate | 10 | 5.6 | Sucrose | 3 | 83.53 |
| 17 | Citric acid-disodium phosphate | 30 | 5 | Sucrose | 3 | 82.61 |
| 18 | Citric acid-disodium phosphate | 30 | 5.6 | Trehalose | 6 | 83.87 |

The Tm value was used as the response value and the model was fitted according to the experimental results. $R^2$ was 0.99987, the adjusted $R^2$ was 0.9979113, and P=0.0348<0.05 in the variance analysis, indicating that the model was effective and the results were reliable.

Note: The unit of the saccharide concentration is in g/100 mL.

Figure 3:
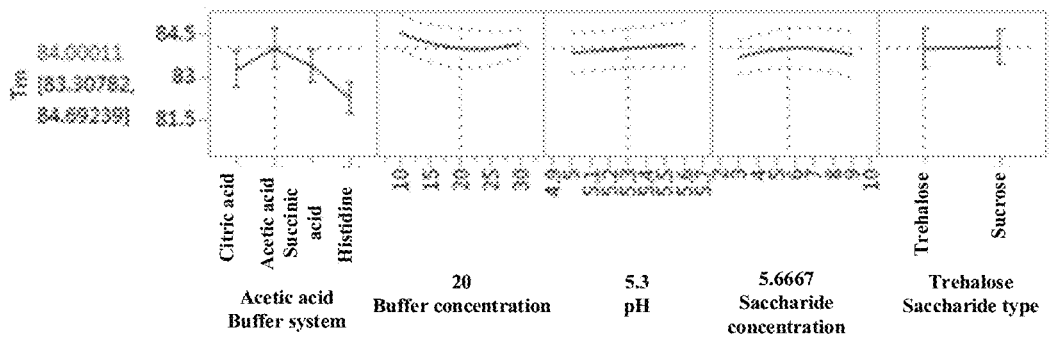
FIG. 3: The main effect plot for Tm factors (including buffer system, the concentration of the buffer, the pH of the pharmaceutical composition, the concentration of the saccharide, and the type of the saccharide).

According to the principle of maximizing the value of Tm, the formulation was preliminarily selected by the main effect diagrams of Tm factors (FIG. 3). For buffer system, (sodium) acetate is better, followed by (sodium) succinate; when buffer concentration is 20-30 mM, the Tm value is higher; pH 5-5.6 had no significant effect on the Tm value; the best saccharide concentration is 6%.

Embodiment 3

The anti-PD-L1 antibody (HRP00052) was formulated into a preparation containing 10 mM (sodium) succinate, (sodium) acetate, 60 mg/mL sucrose and 0.2 mg/mL polysorbate 20 at pH 5.0-5.5, respectively, and the protein concentration was 50 mg/mL. Each preparation was filtered and filled in a neutral borosilicate glass injection vial sealed with a bromobutyl rubber stopper for long-term stability observation at 2-8° C. The stability of the sample was illustrated by the various features shown in Table 3.

The color, appearance and clarity of the sample were determined by visual inspection of the sample under white fluorescent light at room temperature with a black background. The purity of the samples was further evaluated by high performance size exclusion chromatography (HP-SEC), wherein the percentage of monomer as well as the percentage of high molecular weight substance (maybe aggregates) and late eluting peaks (maybe degradation products) were determined. The purity was assessed by revealing the presence of acidic or basic variants using high performance ion exchange chromatography (HP-IEX) and the results were expressed as the percentage of the total observed substance. Samples were analyzed by CE-SDS technique in which proteins were denatured with sodium dodecyl sulfate (SDS) under reducing and non-reducing conditions and separated using capillary electrophoresis (CE). The proteins were separated based on their apparent molecular weight. Under non-reducing conditions, all substances except the main IgG peak were classified as impurities. Under reducing conditions, IgG was split into heavy and light chains, and all other substances were classified as impurities.

The results showed that the stability of anti-PD-L1 antibody in succinate buffer system was significantly better than that of acetate buffer system; and the anti-PD-L1 antibody was very stable at pH 5.0-5.5.

TABLE 3

Effect of pH and buffer system on the long-term stability of PD-L1 antibody at 2-8° C.

| Buffer | pH | Time (months) | Appearance | SEC (area %) | | IEC (area %) | | | CE-SDS (% CPA) | |
|---|---|---|---|---|---|---|---|---|---|---|
| | | | | Monomer | Polymer | Acidic peak | Main peak | Basic peak | Reduced | Non-reduced |
| (sodium) acetate | 5.0 | 0 | Clear and transparent | 98.30 | 1.0 | 21.0 | 63.7 | 15.3 | 97.40 | 96.00 |
| | | 3 | Clear and transparent | 98.30 | 1.0 | 24.1 | 62.2 | 13.7 | 98.76 | 95.30 |
| | | 6 | With smoky fine suspended particles | N/A | N/A | N/A | N/A | N/A | N/A | N/A |
| (sodium) acetate | 5.2 | 0 | Clear and transparent | 98.3 | 1.0 | 21.1 | 63.7 | 15.2 | 97.20 | 96.10 |
| | | 3 | Clear and transparent | 98.2 | 1.1 | 24.1 | 61.8 | 14.0 | 98.74 | 95.45 |
| | | 6 | With smoky fine suspended particles | N/A | N/A | N/A | N/A | N/A | N/A | N/A |
| (sodium) acetate | 5.5 | 0 | Clear and transparent | 98.3 | 1.0 | 21.0 | 64.1 | 15.0 | 97.20 | 96.10 |
| | | 3 | Clear and transparent | 98.2 | 1.1 | 24.0 | 62.4 | 13.6 | 98.76 | 95.41 |
| | | 6 | With smoky fine suspended particles | N/A | N/A | N/A | N/A | N/A | N/A | N/A |
| (sodium) succinate | 5.0 | 0 | Clear and transparent | 98.4 | 1.0 | 21.4 | 63.6 | 14.9 | 97.80 | 96.10 |
| | | 3 | Clear and transparent | 98.3 | 1.0 | 24.4 | 61.5 | 14.1 | 98.65 | 95.85 |
| | | 6 | Clear and transparent | 97.2 | 0.7 | 25.0 | 60.6 | 14.4 | 98.43 | 96.11 |
| (sodium) succinate | 5.2 | 0 | Clear and transparent | 98.2 | 1.0 | 21.9 | 62.5 | 15.6 | 97.40 | 95.80 |
| | | 3 | Clear and transparent | 98.2 | 1.0 | 24.3 | 61.1 | 14.6 | 98.64 | 95.20 |
| | | 6 | Clear and transparent | 97.2 | 0.7 | 24.9 | 60.7 | 14.4 | 98.44 | 96.15 |
| (sodium) succinate | 5.5 | 0 | Clear and transparent | 98.2 | 1.1 | 23.0 | 62.4 | 14.7 | 97.50 | 95.90 |
| | | 3 | Clear and transparent | 98.2 | 1.1 | 24.1 | 61.6 | 14.3 | 98.61 | 95.45 |
| | | 6 | Clear and transparent | 97.2 | 0.7 | 24.9 | 60.6 | 14.5 | 97.66 | 96.19 |

Embodiment 4

The anti-PD-L1 antibody was formulated into a preparation containing 60 mg/mL sucrose and 0.2 mg/mL polysorbate 20 in 10 mM and 20 mM (sodium) succinate at pH 5.2, respectively, and the protein concentration was 50 mg/mL. Each preparation was filtered and filled in a neutral borosilicate glass injection vial sealed with a bromobutyl rubber stopper, followed by acceleration at 40° C. and long-term stability observation at 2-8° C. The results showed that the anti-PD-L1 antibody was quite stable in the 10-20 mM succinate buffer system.

TABLE 4

The stability results of the preparations with different buffer system concentrations at 40° C.

| Concentration | Time (days) | Appearance | SEC (area %) | | IEC (area %) | | | Non-reduced CE-SDS (% CPA) |
| --- | --- | --- | --- | --- | --- | --- | --- | --- |
| | | | Monomer | Polymer | Acidic peak | Main peak | Basic peak | |
| 10 mM | 0 | Clear and transparent | 98.2 | 1.2 | 23.4 | 60.4 | 16.2 | 95.28 |
| | 28 | Clear and transparent | 96.9 | 2.0 | 35.0 | 51.8 | 13.1 | 93.66 |
| 20 mM | 0 | Clear and transparent | 98.1 | 1.2 | 23.5 | 60.9 | 15.6 | 95.30 |
| | 28 | Clear and transparent | 96.8 | 2.1 | 35.5 | 52.2 | 12.3 | 93.74 |

TABLE 5

The stability results of the preparations with different buffer system concentrations at 40° C.

| Concentration | Time (months) | Appearance | SEC (area %) | | IEC (area %) | | | Non-reduced CE-SDS (% CPA) |
| --- | --- | --- | --- | --- | --- | --- | --- | --- |
| | | | Monomer | Polymer | Acidic peak | Main peak | Basic peak | |
| 10 mM | 0 | Clear and transparent | 98.2 | 1.2 | 23.4 | 60.4 | 16.2 | 95.28 |
| | 1 | Clear and transparent | 98.1 | 1.1 | 24.2 | 60.4 | 15.4 | 96.31 |
| | 3 | Clear and transparent | 96.9 | 1.0 | 24.8 | 58.7 | 16.5 | 96.10 |
| | 6 | Clear and transparent | 98.2 | 1.1 | 23.6 | 60.9 | 15.5 | 94.86 |
| 20 mM | 0 | Clear and transparent | 98.1 | 1.2 | 23.5 | 60.9 | 15.6 | 95.30 |
| | 1 | Clear and transparent | 98.0 | 1.1 | 24.2 | 60.2 | 15.6 | 95.78 |
| | 3 | Clear and transparent | 96.9 | 1.0 | 24.9 | 58.7 | 16.4 | 96.05 |
| | 6 | Clear and transparent | 98.2 | 1.1 | 23.3 | 61.5 | 15.2 | 95.70 |

Embodiment 5

The anti-PD-L1 antibody preparations containing 50 mg/mL PD-LI antibody (HRP00052), 20 mM (sodium) acetate at pH 5.2 and 60 mg/mL sucrose, and different types and concentrations of surfactant were prepared. Each preparation was filtered and filled in a neutral borosilicate glass injection vial sealed with a bromobutyl rubber stopper and placed on a 25° C. constant temperature shaker, and shaken at 200 rpm.

DLS (Dynamic Light Scattering) was used to measure the average diffusion coefficient, which was used to characterize the particle size and particle size distribution of nano-sized particles in solution. PDI (particle dispersion index) distribution coefficient reflects the uniformity of particle size. The lower the PDI value, the narrower the particle size distribution and the more uniform the particle size.

The stability results indicated that 0.1-0.3 mg/mL polysorbate 20 or polysorbate 80 effectively prevented the aggregation of anti-PD-L1 antibodies and the formation of agglomerated large particles.

TABLE 6

Results of shaking test of different types and concentrations of polysorbate

| Type | Concentration (mg/mL) | Time (days) | Appearance | DLS (nm) Z-Ave Mean | PDI | SEC (area %) Monomer | Polymer |
|---|---|---|---|---|---|---|---|
| Without polysorbate | 0 | 0 | Clear and transparent | 17.27 | 0.29 | 98.8 | 1.2 |
| | | 3 | Turbid | 16.23 | 0.25 | 98.2 | 1.3 |
| | | 7 | Turbid | 15.41 | 0.25 | 97.9 | 1.4 |
| Polysorbate 20 | 0.1 | 0 | Clear and transparent | 13.98 | 0.13 | 98.7 | 1.3 |
| | | 3 | With suspended particles occasionally | 14.08 | 0.13 | 98.2 | 1.3 |
| | | 7 | With suspended particles occasionally | 13.80 | 0.10 | 97.8 | 1.4 |
| Polysorbate 20 | 0.2 | 0 | Clear and transparent | 14.08 | 0.14 | 98.7 | 1.3 |
| | | 3 | With suspended particles occasionally | 14.13 | 0.14 | 98.0 | 1.4 |
| | | 7 | With suspended particles occasionally | 13.82 | 0.09 | 97.8 | 1.5 |
| Polysorbate 20 | 0.3 | 0 | Clear and transparent | 14.13 | 0.14 | 98.7 | 1.3 |
| | | 3 | With suspended particles occasionally | 13.90 | 0.13 | 98.1 | 1.3 |
| | | 7 | With suspended particles occasionally | 14.13 | 0.15 | 97.8 | 1.5 |
| Polysorbate 80 | 0.1 | 0 | Clear and transparent | 14.22 | 0.16 | 98.7 | 1.3 |
| | | 3 | With suspended particles occasionally | 14.07 | 0.12 | 98.1 | 1.4 |
| | | 7 | With suspended particles occasionally | 15.08 | 0.17 | 98.0 | 1.3 |
| Polysorbate 80 | 0.2 | 0 | Clear and transparent | 14.51 | 0.18 | 98.7 | 1.3 |
| | | 3 | With suspended particles occasionally | 13.73 | 0.10 | 98.2 | 1.2 |
| | | 7 | With suspended particles occasionally | 14.15 | 0.13 | 97.4 | 1.9 |
| Polysorbate 80 | 0.3 | 0 | Clear and transparent | 13.74 | 0.12 | 98.8 | 1.2 |
| | | 3 | With suspended particles occasionally | 14.10 | 0.14 | 98.3 | 1.2 |
| | | 7 | With suspended particles occasionally | 14.15 | 0.13 | 97.9 | 1.4 |

Embodiment 6

The anti-PD-L1 antibody preparations containing 50 mg/mL PD-LI antibody (HRP00052), 20 mM (sodium) succinate at pH 5.2 and 60 mg/mL sucrose, and different types and concentrations of surfactant were prepared. Each preparation was filtered and filled in a neutral borosilicate glass injection vial sealed with a bromobutyl rubber stopper and placed at 2-8° C. for stability test. The results showed that polysorbate 80 was significantly better than polysorbate 20, and there was no significant difference between each concentration.

TABLE 7

The stability results of the preparations with different types and concentrations of polysorbate at 2-8° C.

| Type | Concentration mg/mL | Time (months) | Appearance | SEC (area %) Monomer | SEC (area %) Polymer | IEC (area %) Acidic peak | IEC (area %) Main peak | IEC (area %) Basic peak | Non-reduced CE-SDS (% CPA) |
|---|---|---|---|---|---|---|---|---|---|
| Polysorbate | 0.2 | 0 | Clear and transparent | 98.1 | 1.20 | 24.3 | 60.5 | 15.2 | 95.9 |
| | | 3 | With fine suspended particles | N/A | N/A | 24.5 | 59.6 | 15.9 | 96.6 |
| | | 6 | With visible suspended particles | 98.3 | 1.15 | 23.8 | 60.3 | 15.9 | 96.2 |
| | 0.4 | 0 | Clear and transparent | 98.2 | 1.20 | 24.4 | 59.4 | 16.2 | 96.0 |
| | | 3 | With fine suspended particles | N/A | N/A | 24.7 | 59.5 | 15.8 | 95.9 |
| | | 6 | With visible suspended particles | 98.2 | 1.17 | 23.6 | 58.7 | 17.7 | 95.9 |
| | 0.6 | 0 | Clear and transparent | 98.1 | 1.20 | 24.3 | 60.2 | 15.5 | 95.3 |
| | | 3 | Clear and transparent | N/A | N/A | 24.6 | 59.3 | 16.1 | 95.9 |
| | | 6 | With visible suspended particles | 98.3 | 1.16 | 24.1 | 60.0 | 15.9 | 95.9 |
| Polysorbate 80 | 0.4 | 0 | Clear and transparent | 98.1 | 1.20 | 23.7 | 60.5 | 15.8 | 96.0 |
| | | 3 | Clear and transparent | N/A | N/A | 24.7 | 59.5 | 15.8 | 95.3 |
| | | 6 | Clear and transparent | 98.3 | 1.17 | 23.3 | 58.7 | 18.0 | 95.8 |
| | 0.6 | 0 | Clear and transparent | 98.2 | 1.10 | 24.7 | 59.8 | 15.5 | 94.8 |
| | | 3 | Clear and transparent | N/A | N/A | 25.0 | 58.7 | 16.3 | 96.6 |
| | | 6 | Clear and transparent | 98.3 | 1.15 | 23.6 | 58.5 | 17.9 | 95.7 |
| | 0.8 | 0 | Clear and transparent | 98.1 | 1.20 | 24.2 | 59.8 | 16.0 | 95.7 |
| | | 3 | Clear and transparent | N/A | N/A | 24.8 | 59.4 | 15.9 | 95.7 |
| | | 6 | Clear and transparent | 98.3 | 1.14 | 23.9 | 59.9 | 16.2 | 95.4 |

What is claimed is:

1. A pharmaceutical composition, comprising:
   (a) 30 mg/mL-80 mg/mL anti-PD-L1 antibody or antigen-binding fragment thereof;
   (b) 5 mM-50 mM succinate buffer at pH 4.5-6.0;
   (c) 30 mg/mL-90 mg/mL disaccharide, wherein the disaccharide is sucrose or trehalose; and
   (d) 0.1 mg/mL-1.0 mg/mL polysorbate 80; wherein, the anti-PD-L1 antibody or the antigen-binding fragment thereof comprises light chain complementary determining regions LCDR1, LCDR2 and LCDR3, and heavy chain complementary determining regions HCDR1, HCDR2 and HCDR3, wherein:
   HCDR1 is SYWMH (SEQ ID NO: 7),
   HCDR2 is RIX$_4$PNSG X$_5$TSYNEKFKN (SEQ ID NO: 8),
   HCDR3 is GGSSYDYFDY (SEQ ID NO: 9),
   LCDR1 is RASESVSIHGTHLMH (SEQ ID NO: 10),
   LCDR2 is AASNLES (SEQ ID NO: 11),
   LCDR3 is QQSFEDPLT (SEQ ID NO: 12),
   wherein X$_4$ is selected from H or G, and X$_5$ is selected from G or F.

2. The pharmaceutical composition of claim 1, wherein the pharmaceutical composition has a pH of 5.0 to 6.0.

3. The pharmaceutical composition of claim 1, wherein the buffer has a concentration of 10 mM to 30 mM.

4. The pharmaceutical composition of claim 1, wherein the antibody or the antigen binding fragment thereof has a concentration of 40 mg/mL to 60 mg/mL.

5. The pharmaceutical composition of claim 1, wherein the disaccharide has a concentration of 40 mg/mL to 80 mg/mL.

6. The pharmaceutical composition of claim 1, wherein the polysorbate 80 has a concentration of 0.4 mg/mL to 0.8 mg/mL.

7. The pharmaceutical composition of claim 1 comprising:
   (a) 45 mg/mL-55 mg/mL of the anti-PD-L1 antibody or the antigen-binding fragment thereof;
   (b) 10 mM-20 mM succinate buffer at pH 5.0-6.0;
   (c) 55 mg/mL-65 mg/mL sucrose; and
   (d) 0.15 mg/mL-0.8 mg/mL polysorbate 80.

8. The pharmaceutical composition of claim 1, wherein the pharmaceutical composition is selected from one of the following compositions:
   (a) 50 mg/mL of the anti-PD-L1 antibody or the antigen-binding fragment thereof, 20 mM succinate buffer at pH 5.2, 60 mg/mL sucrose and 0.4 mg/mL polysorbate 80;
   (b) 50 mg/mL of the anti-PD-L1 antibody or the antigen-binding fragment thereof, 20 mM succinate buffer at pH 5.2, 60 mg/mL sucrose and 0.6 mg/mL polysorbate 80;
   (c) 50 mg/mL of the anti-PD-L1 antibody or the antigen-binding fragment thereof, 20 mM succinate buffer at pH 5.2, 60 mg/mL sucrose and 0.8 mg/mL polysorbate 80;
   (d) 50 mg/mL of the anti-PD-L1 antibody or the antigen-binding fragment thereof, 20 mM succinate buffer at pH 5.5, 60 mg/mL sucrose and 0.6 mg/mL polysorbate 80;
   (e) 50 mg/mL of the anti-PD-L1 antibody or the antigen-binding fragment thereof, 20 mM succinate buffer at pH 5.8, 60 mg/mL sucrose and 0.6 mg/mL polysorbate 80.

9. The pharmaceutical composition of to claim 1, wherein the anti-PD-L1 antibody or the antigen-binding fragment thereof is selected from the group consisting of a murine antibody, a chimeric antibody, a humanized antibody and a human antibody.

10. The pharmaceutical composition of claim 1, wherein the anti-PD-L1 antibody or the antigen-binding fragment thereof has a heavy chain variable region sequence that is shown in SEQ ID NO: 13, and a light chain variable region sequence that is shown in SEQ ID NO: 14.

11. The pharmaceutical composition of claim 1, wherein the anti-PD-L1 antibody or the antigen-binding fragment thereof has a heavy chain sequence that is shown in SEQ ID NO: 15, and a light chain sequence that is shown in SEQ ID NO: 17.

12. A method for preparing the pharmaceutical composition of claim 1, comprising mixing the anti-PD-L1 antibody or antigen-binding fragment thereof with a pharmaceutically acceptable excipient.

13. A pharmaceutical composition, comprising:
   (a) 45 mg/mL-55 mg/mL anti-PD-L1 antibody or antigen-binding fragment thereof;
   (b) 10 mM-20 mM succinate buffer at pH 5.0-6.0;
   (c) 55 mg/mL-65 mg/mL sucrose; and
   (d) 0.1 mg/mL-0.8 mg/mL polysorbate 80,
   wherein the anti-PD-L1 antibody or the antigen-binding fragment thereof comprises a heavy chain variable region of SEQ ID NO: 13, and a light chain variable region of SEQ ID NO: 14.

14. A pharmaceutical composition, comprising:
50 mg/mL anti-PD-L1 antibody;
20 mM succinate buffer at pH 5.2;
60 mg/mL sucrose; and 0.6 mg/mL polysorbate 80,
wherein the anti-PD-L1 antibody comprises a heavy chain of SEQ ID NO: 15, and a light chain of SEQ ID NO: 17.

* * * * *

SEQUENCE LISTING

<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: HCDR1 of antibody 1
<220> FEATURE:
<221> NAME/KEY: UNSURE
<222> LOCATION: (5)..(5)
<223> OTHER INFORMATION: Xaa is N or T.

```
<220> FEATURE:
<221> NAME/KEY: UNSURE
<222> LOCATION: (5)..(5)
<223> OTHER INFORMATION: The 'Xaa' at location 5 stands for Asn or Thr.

<400> SEQUENCE: 1

Asn Asp Tyr Trp Xaa
1               5

<210> SEQ ID NO 2
<211> LENGTH: 16
<212> TYPE: PRT
<213> ORGANISM: Artificial Sequence
<220> FEATURE:
<223> OTHER INFORMATION: HCDR2 of antibody 1

<400> SEQUENCE: 2

Tyr Ile Ser Tyr Thr Gly Ser Thr Tyr Tyr Asn Pro Ser Leu Lys Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: PD-L1 (ECD)-Flag-His6

<400> SEQUENCE: 3

Ser Gly Gly Trp Leu Ala Pro Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: LCDR1 of antibody 1
<220> FEATURE:
<221> NAME/KEY: UNSURE
<222> LOCATION: (9)..(9)
<223> OTHER INFORMATION: The 'Xaa' at location 9 stands for Arg or His.
<220> FEATURE:
<221> NAME/KEY: UNSURE
<222> LOCATION: (14)..(14)
<223> OTHER INFORMATION: Xaa is N or H.
<220> FEATURE:
<221> NAME/KEY: UNSURE
<222> LOCATION: (14)..(14)
<223> OTHER INFORMATION: The 'Xaa' at location 14 stands for Asn or His.

<400> SEQUENCE: 4

Lys Ser Ser Gln Ser Leu Phe Tyr Xaa Ser Asn Gln Lys Xaa Ser Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: LCDR2 of antibody 1

<400> SEQUENCE: 5

Gly Ala Ser Thr Arg Glu Ser
1               5

<210> SEQ ID NO 6
<211> LENGTH: 9
```

```
<212> TYPE: PRT
<213> ORGANISM: Artificial Sequence
<220> FEATURE:
<223> OTHER INFORMATION: LCDR3 of antibody 1

<400> SEQUENCE: 6

Gln Gln Tyr Tyr Gly Tyr Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1 of antibody 2

<400> SEQUENCE: 7

Ser Tyr Trp Met His
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2 of antibody 2
<220> FEATURE:
<221> NAME/KEY: UNSURE
<222> LOCATION: (3)..(3)
<223> OTHER INFORMATION: Xaa is H or G.
<220> FEATURE:
<221> NAME/KEY: UNSURE
<222> LOCATION: (3)..(3)
<223> OTHER INFORMATION: The 'Xaa' at location 3 stands for His or Gly.
<220> FEATURE:
<221> NAME/KEY: UNSURE
<222> LOCATION: (8)..(8)
<223> OTHER INFORMATION: Xaa is G or F.
<220> FEATURE:
<221> NAME/KEY: UNSURE
<222> LOCATION: (8)..(8)
<223> OTHER INFORMATION: The 'Xaa' at location 8 stands for Gly or Phe.

<400> SEQUENCE: 8

Arg Ile Xaa Pro Asn Ser Gly Xaa Thr Ser Tyr Asn Glu Lys Phe Lys
1               5                   10                  15

Asn

<210> SEQ ID NO 9
<211> LENGTH: 10
<212> TYPE: PRT
<213> ORGANISM: Artificial Sequence
<220> FEATURE:
<223> OTHER INFORMATION: HCDR3 of antibody 2

<400> SEQUENCE: 9

Gly Gly Ser Ser Tyr Asp Tyr Phe Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: LCDR1 of antibody 2

<400> SEQUENCE: 10

Arg Ala Ser Glu Ser Val Ser Ile His Gly Thr His Leu Met His
1               5                   10                  15
```

<210> SEQ ID NO 11
<211> LENGTH: 7
<212> TYPE: PRT
<213> ORGANISM: Artificial Sequence
<220> FEATURE:
<223> OTHER INFORMATION: LCDR2 of antibody 2

<400> SEQUENCE: 11

Ala Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3 of antibody 2

<400> SEQUENCE: 12

Gln Gln Ser Phe Glu Asp Pro Leu Thr
1               5

<210> SEQ ID NO 13
<211> LENGTH: 119
<212> TYPE: PRT
<213> ORGANISM: Artificial Sequence
<220> FEATURE:
<223> OTHER INFORMATION: heavy chain variable region sequence of
      humanized antibody 2 after affinity maturation

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 14
<211> LENGTH: 111
<212> TYPE: PRT
<213> ORGANISM: Artificial Sequence
<220> FEATURE:
<223> OTHER INFORMATION: Light chain variable region of humanized
      antibody 2 after affinity maturation

<400> SEQUENCE: 14

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
            35                  40                  45

Lys Leu Leu Ile Tyr Ala Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Glu Asp Thr Ala Asn Tyr Tyr Cys Gln Gln Ser Phe
                 85                  90                  95

Glu Asp Pro Leu Thr Phe Gly Gln Gly Thr Lys Leu Glu Ile Lys
                100                 105                 110

<210> SEQ ID NO 15
<211> LENGTH: 446
<212> TYPE: PRT
<213> ORGANISM: Artificial Sequence
<220> FEATURE:
<223> OTHER INFORMATION: Heavy chain sequence of HRP00052 antibody

<400> SEQUENCE: 15

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
 50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

```
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 16
<211> LENGTH: 1341
<212> TYPE: DNA
<213> ORGANISM: Artificial Sequence
<220> FEATURE:
<223> OTHER INFORMATION: Heavy chain sequence encoding gene sequence of
      HRP00052 antibody

<400> SEQUENCE: 16
caggtgcaac tggtgcagag cggtgccgag gtgaagaagc tggcgcaag cgtgaaagtg      60 agctgcaagg ccagcggcta caccttcacc agctactgga tgcactgggt gaggcaggcc    120
cctggacagg gcctggagtg gatgggcagg atcgggccca cagtggtttt cactagctac    180
aatgaaaagt tcaagaacag gtaaccatg accagggaca cctccaccag cacagtgtat    240
atggagctga gcagcctgag gagcgaggac accgccgtgt actactgtgc cagaggcggc    300
agcagctacg actacttcga ctattgggggc cagggcacca ccgtgaccgt gagcagtgct    360
tccaccaagg gcccatcggt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc atgcccagca cctgaggctg ctggggacc atcagtcttc    720 ctgttccccc caaaacccaa ggacactctc atgatctccc ggaccctga ggtcacgtgc     780 gtggtggtgg acgtgagcca ggaagacccc gaggtccagt tcaactggta cgtggatggc    840
gtggaggtgc ataatgccaa gacaaagccg cggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaagggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
```

```
gagagcaatg ggcagccgga gaacaactac aagaccacgc ctcccgtgct ggactccgac    1200
ggctccttct tcctctacag caggctcacc gtggacaaga gcaggtggca ggagggaat    1260 gtcttctcat gctccgtgat gcatgaggct ctgcacaacc actacacaca gaagagcctc    1320
tccctgtctc tgggtaaatg a                                               1341
```

<210> SEQ ID NO 17
<211> LENGTH: 218
<212> TYPE: PRT
<213> ORGANISM: Artificial Sequence
<220> FEATURE:
<223> OTHER INFORMATION: Light chain sequence of HRP00052 antibody

<400> SEQUENCE: 17

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 18
<211> LENGTH: 657
<212> TYPE: DNA
<213> ORGANISM: Artificial Sequence
<220> FEATURE:
<223> OTHER INFORMATION: Light chain sequence encoding gene sequence of
      HRP00052 antibody

<400> SEQUENCE: 18

```
gacatcgtgc tgacccagag tcccgcctca cttgccgtga gccccggtca gagggccacc    60
atcacctgta gggccagcga gagcgtgagc atccacggca cccacctgat gcactggtat    120
caacagaaac ccggccagcc ccccaaactg ctgatctacg ccgccagcaa cctggagagc    180
ggcgtgcccg ccaggttcag cggctccggc agcggcaccg acttcaccct cactatcaac    240
```

```
cccgtggagg ccgaggacac cgccaactac tactgccagc agagcttcga ggaccccctg      300
accttcggcc agggcaccaa gctggagatc aagcgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgttga          657
```

<210> SEQ ID NO 19
<211> LENGTH: 290
<212> TYPE: PRT
<213> ORGANISM: Artificial Sequence
<220> FEATURE:
<223> OTHER INFORMATION: Human PD-L1 full-length amino acid sequence

<400> SEQUENCE: 19

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
```

-continued

290

<210> SEQ ID NO 20
<211> LENGTH: 242
<212> TYPE: PRT
<213> ORGANISM: Artificial Sequence
<220> FEATURE:
<223> OTHER INFORMATION: PD-L1 with His, PADRE tag

<400> SEQUENCE: 20

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Ser Gly Ala
    210                 215                 220

Lys Phe Val Ala Ala Trp Thr Leu Lys Ala Ala Ala His His His His
225                 230                 235                 240

His His

<210> SEQ ID NO 21
<211> LENGTH: 234
<212> TYPE: PRT
<213> ORGANISM: Artificial Sequence
<220> FEATURE:
<223> OTHER INFORMATION: PD-L1 with FLAG, HIS tag: PD-L1(ECD)-Flag-His6

<400> SEQUENCE: 21

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg

```
            50                  55                  60
Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Asp Tyr Lys Asp
    210                 215                 220

Asp Asp Asp Lys His His His His His His
225                 230

<210> SEQ ID NO 22
<211> LENGTH: 447
<212> TYPE: PRT
<213> ORGANISM: Artificial Sequence
<220> FEATURE:
<223> OTHER INFORMATION: Fc fusion protein of PD-L1: PD-L1(ECD)-Fc

<400> SEQUENCE: 22

Phe Thr Val Thr Val Pro Lys Asp Leu Tyr Val Val Glu Tyr Gly Ser
 1                   5                  10                  15

Asn Met Thr Ile Glu Cys Lys Phe Pro Val Glu Lys Gln Leu Asp Leu
                 20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
```

```
                    180                 185                 190
Phe Arg Arg Leu Asp Pro Glu Glu Asn His Thr Ala Glu Leu Val Ile
            195                 200                 205
Pro Glu Leu Pro Leu Ala His Pro Pro Asn Glu Arg Asp Lys Thr His
        210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 23
<211> LENGTH: 382
<212> TYPE: PRT
<213> ORGANISM: Artificial Sequence
<220> FEATURE:
<223> OTHER INFORMATION: Fc fusion protein of PD-L1: PD-1(ECD)-Fc

<400> SEQUENCE: 23

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Ser Phe Val Leu Asn Trp Tyr
            35                  40                  45
Arg Met Ser Pro Ser Asn Gln Thr Asp Lys Leu Ala Ala Phe Pro Glu
        50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
```

-continued

```
              100                 105                 110
Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Glu Pro Lys Ser Ser Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Tyr Thr Leu Pro Pro
                275                 280                 285

Ser Arg Asp Glu Leu Thr Lys Asn Gln Val Ser Leu Thr Cys Leu Val
                290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys
                370                 375                 380

<210> SEQ ID NO 24
<211> LENGTH: 118
<212> TYPE: PRT
<213> ORGANISM: Artificial Sequence
<220> FEATURE:
<223> OTHER INFORMATION: 1 hVH- CDR graft

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
                20                  25                  30

Tyr Trp Asn Trp Ile Arg Gln His Pro Gly Lys Gly Leu Glu Trp Ile
            35                  40                  45

Gly Tyr Ile Ser Tyr Thr Gly Ser Thr Tyr Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                 85                  90                  95

Arg Ser Gly Gly Trp Leu Ala Pro Phe Asp Tyr Trp Gly Arg Gly Thr
            100                 105                 110

Leu Val Thr Val Ser Ser
        115

<210> SEQ ID NO 25
<211> LENGTH: 113
<212> TYPE: PRT
<213> ORGANISM: Artificial Sequence
<220> FEATURE:
<223> OTHER INFORMATION: 1 hVL CDR graft

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Arg
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys

<210> SEQ ID NO 26
<211> LENGTH: 119
<212> TYPE: PRT
<213> ORGANISM: Artificial Sequence
<220> FEATURE:
<223> OTHER INFORMATION: 2- hVH.1

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile His Pro Asn Ser Gly Gly Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 27
<211> LENGTH: 111
<212> TYPE: PRT
```

```
<213> ORGANISM: Artificial Sequence
<220> FEATURE:
<223> OTHER INFORMATION: 2-hVL.1

<400> SEQUENCE: 27

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Phe
                85                  90                  95

Glu Asp Pro Leu Thr Phe Gly Gly Thr Lys Leu Glu Ile Lys
            100                 105                 110

<210> SEQ ID NO 28
<211> LENGTH: 118
<212> TYPE: PRT
<213> ORGANISM: Artificial Sequence
<220> FEATURE:
<223> OTHER INFORMATION: Humanized antibody 1 heavy chain variable
      region after affinity maturation

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Tyr Ile Ser Tyr Thr Gly Ser Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
        115

<210> SEQ ID NO 29
<211> LENGTH: 113
<212> TYPE: PRT
<213> ORGANISM: Artificial Sequence
<220> FEATURE:
<223> OTHER INFORMATION: Humanized antibody 1 light chain variable
      region after affinity maturation

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
            20                  25                  30
```

-continued

```
Ser Asn Gln Lys His Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys
```